United States Patent
Pedtke et al.

(10) Patent No.: US 10,206,795 B2
(45) Date of Patent: Feb. 19, 2019

(54) PROSTHETIC SUPPORT SOCKET FOR AN OSSEOINTEGRATED FEMORAL ABUTMENT

(71) Applicant: LIM Innovations, Inc., San Francisco, CA (US)

(72) Inventors: Andrew C. Pedtke, San Francisco, CA (US); Loren Maxwell Brock, Sebastopol, CA (US); Davindra Mark Sethi, Tiburon, CA (US); Preston Fung, South San Francisco, CA (US); Jesse Robert Williams, San Francisco, CA (US); Garrett Ray Hurley, San Francisco, CA (US)

(73) Assignee: LIM Innovations, Inc., San Francisco, CA (US)

( * ) Notice: Subject to any disclaimer, the term of this patent is extended or adjusted under 35 U.S.C. 154(b) by 0 days.

(21) Appl. No.: 15/220,050

(22) Filed: Jul. 26, 2016

(65) Prior Publication Data

US 2017/0027720 A1 Feb. 2, 2017

Related U.S. Application Data

(60) Provisional application No. 62/197,427, filed on Jul. 27, 2015, provisional application No. 62/267,820, (Continued)

(51) Int. Cl.
*A61F 2/60* (2006.01)
*A61F 2/80* (2006.01)
(Continued)

(52) U.S. Cl.
CPC .............. *A61F 2/80* (2013.01); *A61F 2/2814* (2013.01); *A61F 2/78* (2013.01);
(Continued)

(58) Field of Classification Search
CPC ........ A61F 2/60; A61F 2/80; A61F 2002/785; A61F 2002/7843
See application file for complete search history.

(56) References Cited

U.S. PATENT DOCUMENTS

| | | | |
|---|---|---|---|
| 8,444,701 B2 * | 5/2013 | Bloebaum | A61F 2/2814 623/32 |
| 2008/0161938 A1 * | 7/2008 | Gramnas | A61F 2/60 623/33 |
| 2016/0000587 A1 * | 1/2016 | Hurley | A61F 2/80 623/35 |

FOREIGN PATENT DOCUMENTS

| | | |
|---|---|---|
| DE | 319623 | 3/1920 |
| EP | 204407 | 12/1986 |

(Continued)

OTHER PUBLICATIONS

Allard USA, "Cut-4-Custom: Custom TLSO in Less Than an Hour," O&P Edge Magazine, downloaded from the internet: <URL: http://www.oandp.com/articles/news_2010-07-01_24.asp>, 2 pages, Jul. 2010.

(Continued)

*Primary Examiner* — Bruce E Snow
(74) *Attorney, Agent, or Firm* — Gordon & Jacobson, P.C.

(57) ABSTRACT

An osseointegrated abutment support socket for a residual limb in which an osseointegrated abutment has been implanted is described. The osseointegrated abutment support socket may include a distal socket base assembly, multiple longitudinal struts and a percutaneous site protector. The distal socket base assembly may include a base plate, a collar extending proximally from the base plate and forming a receptacle for receiving a distal end of the osseointegrated abutment, and a strut support ring disposed around the collar. The struts are connected at their distal ends (Continued)

to the strut support ring and extend proximally upward. The percutaneous site protector contacts a distal surface of the residual limb near a percutaneous site where the distal end of the osseointegrated abutment exits the residual limb.

19 Claims, 17 Drawing Sheets

Related U.S. Application Data filed on Dec. 15, 2015, provisional application No. 62/364,930, filed on Jul. 21, 2016.

(51) Int. Cl.

| | | |
|---|---|---|
| A61F 2/28 | (2006.01) | |
| A61F 2/78 | (2006.01) | |
| A61F 2/50 | (2006.01) | |
| A61F 2/74 | (2006.01) | |
| A61F 2/76 | (2006.01) | |

(52) U.S. Cl.
CPC ... A61F 2002/501 (2013.01); A61F 2002/503 (2013.01); A61F 2002/5027 (2013.01); A61F 2002/5039 (2013.01); A61F 2002/74 (2013.01); A61F 2002/742 (2013.01); A61F 2002/7615 (2013.01); A61F 2002/7862 (2013.01); A61F 2002/7887 (2013.01)

(56) References Cited

FOREIGN PATENT DOCUMENTS

| EP | 1433447 | 6/2004 |
|---|---|---|
| GB | 127451 | 6/1919 |
| GB | 2080114 | 2/1982 |
| WO | 1991016019 | 10/1991 |
| WO | 1998012994 | 4/1998 |
| WO | 2000003665 | 1/2000 |
| WO | 2000030572 | 6/2000 |
| WO | 2007035875 | 3/2007 |
| WO | 2008116025 | 9/2008 |
| WO | 2009093020 | 7/2009 |
| WO | 2012021823 | 2/2012 |
| WO | 2014004709 | 1/2014 |
| WO | 2014068269 | 5/2014 |

OTHER PUBLICATIONS

Alley, "The high-fidelity interface: Skeletal stabilization through alternating soft tissue compression and release," Myoelectric Symposium, Aug. 14-19, 2011 (3 pages).
Andrysek, "Lower-limb prosthetic technologies in the developing world: a review of literature from 1994-2010," Prosthetics and orthotics international, 34(4):378-398, Dec. 1, 2010.
Burgess et al., "The Management of Lower-Extremity Amputation: Surgery: Immediate Postsurgical Prosthetic Fitting: Patient Care," Superintendent of Documents, U.S. Government Printing Office, Washington D.C., publication prepared for the Prosthetic and Sensory Aids Service Dept of Medicine and Surgery, Veterans Administration, Aug. 1969 (129 pages).
Comfil (thermoformable composite technique). Fillauer Fabrication Manuel. Jun. 15, 2012.
Compton et al., "New plastics for forming directly on the patient*," Prosthetics and orthotics international, 2(1):43-47, Apr. 1978.
Conn, "Materials Science: A look at Some of the Substances on the Market for Device Fabrication," O&P Almanac, pp. 28-31, Jun. 2012.
Fairley, "From Academia to the Developing World," downloaded from <http://www.oandp.com/articles/2011-05_03.asp>, The O&P Edge, 5 pages, May 2011.
Fairley, "M.A.S. Socket: A Transfemoral Revolution," downloaded from <http://www.oandp.com/articles/2004-06_03.asp>, The O&P Edge, 3 pages, Jun. 2004.
Fairley, "Socket can be fabricated, modified, fitted-in one hour," downloaded from <http://www.oandp.com/articles/2007-06_09.asp>, The O&P Edge, 3 pages, Jun. 2007.
Fillauer LLC and Centri® "Comfil® Thermo Formable Composite Technique" Fillauer Fabrication Manuel, 14 pages, Jun. 15, 2012.
Gard, "Overview of Lower Limb Prosthetics Research," WRAMC and the VA Orthopedic & Prosthetic Workshop, Arlington, VA, 49 slides, Nov. 17, 2003.
Geil, "Consistency, precision, and accuracy of optical and electromagnetic shape-capturing systems for digital measurement of residual-limb anthropometrics of persons with transtibial amputation," J Rehabil Res Dev., 44(4):515-524, May 20, 2007.
Gerschutz et al., "Mechanical Evaluation of Direct Manufactured Prosthetic Sockets," American Academy of Orthotists & Prosthetists, 38th Academy Annual Meeting and Scientific Symposium, USA, <URL: http://oandp.org/publications/iop/2012/2012-19.pdf>, 1 pages, Mar. 21, 2012.
Gleave, "A plastic socket and stump casting technique for above-knee prostheses," J Bone Joint Surg Br., 47:100-103, Feb. 1965.
Greenwald et al., "Volume Management: Smart Variable Geometry Socket (SVGS) Technology for Lower-Limb Prostheses," JPO: Journal of Prosthetics and Orthotics, 15(3):107-112, Jul. 1, 2003.
Hanger Inc., "ComfortFlex Socket System," downloaded from http://www.hanger.com/prosthetics/services/Technology/Pages/ComfortFlex.aspx, 2 pages, archived Sep. 17, 2012.
Hanger Prosthetics & Orthotics [online] "ComfortFlex Socket System," downloaded from the internet: <URL: http://www.hanger.com/prosthetics/services/Technology/Pages/ComfortFlex.aspx> on Nov. 28, 2012, 2 pages.
Hong et al., "Dynamic moisture vapor transfer through textiles part I: clothing hygrometry and the influence of fiber type," Textile Research Journal, 58(12):697-706, Dec. 1, 1988 [abstract only].
Hwang [designer], "Blooming Winner-Spark!" Spark Galleries, 3 pages, 2012.
Instamorph, "Moldable Plastic: Instructions" downloaded from URL: <http://www.instamorph.com/instructions>, 2 pages, archived Dec. 24, 2011.
Instamorph: "Remoldable prosthetics"; Apr. 2013, <www.instamorph.com/ideas/outdoors-and-ergonomics/remoldable-prosthetics>.
Jana, "Designing a cheaer, simpler prosthetic arm," ZDNet [online], <URL: http://www.zdnet.com/article/designing-a-cheaper-simpler-prosthetic-arm/> 3 pages, Nov. 14, 2011.
Koike et al., "The TC double socket above-knee prosthesis," Prosthet Orthot Int., 5(3):129-134, Dec. 1981.
Krouskop et al., "Computer-aided design of a prosthetic socket for an above-knee amputee," J Rehabil Res Dev., 24(2):31-38, 1987.
Manucharian, "An investigation of comfort level trend differences between the hands-on patellar tendon bearing and hands off hydrocast transtibial prosthetic sockets," J Prosthet Orthot., 23(3):124-140, Jul. 1, 2011.
Ottobock, "Initial and interim prostheses" Prosthetics Lower Extremities 2008, downloaded from the internet: <URL: http://www.ottobockus.com/cps/rde/xbcr/ob_us_en/08cat_4.pdf> on Feb. 2013, pp. 24-26.
Ottobock, "PU Resin Kit Polytol®" downloaded from the internet: <URL: http://www.ottobock.com/cps/rde/xchg/ob_com_en/hs.xsl/17414.html> on Dec. 17, 2012, 2 pages.
Quigley, "Prosthetics Management: Overview, Methods and Materials," Chapter 4, Atlas of Limb Prosthetics: Surgical, Prosthetic, and Rehabilitation Principles, (Second Edition), 19 pages, 1992.
Sanders et al., "Residual limb volume change: Systematic review of measurement and management," J Rehabil Res Dev., 48(8):949-986, 2011.
Sathishkumar et al., "A cost-effective, adjustable, femoral socket, temporary prosthesis for immediate rehabilitation of above-knee amputation," Int J Rehabil Res., 27(1):71-74, Mar. 1, 2004 [abstract only].
Sbir, "Pro-Active Dynamic Accommodating Socket" Solicitation Topic Code: OSD08-H18, 2 pages, Solicitation Year: 2008.

(56) References Cited

OTHER PUBLICATIONS

Smith, "Silver Linings for O&P Devices" The Academy TODAY, 1(4):A-8-A-9, Oct. 2005.
Spaeth, "Laser imaging and computer-aided design and computer-aided manufacture in prosthetics and orthotics," Phys Med Rehabil Clin N Am., 17(1):245-263, Feb. 28, 2006 [abstract only].
Turner, "Fit for Everyone," Yanko Design [online], <URL:http://www.yankodesign.com/2013/07/17/fit-for-everyone/>, 7 pages, Jul. 17, 2013.
Wilson et al., "Recent advances in above-knee prosthetics," Artif. Limbs., 12(2):1-27, Jan. 1, 1968.
Wilson Jr., "A material for direct forming of prosthetic sockets," Artif. Limbs., 14(1):53-56, Jan. 1, 1970.
Wu et al., "Technical note: CIR sand casting system for trans-tibial socket," Prosthet Orthot Int., 27(2):146-152, Aug. 2003.
Zhang, "Ethylene-vinyl acetate copolymer based on a continuous phase of dual/polycaprolactone blend of the porous material prepared," Yangzhou University, Materials Science, Master's Thesis, [USPTO translation of relevant portions of Zhang article], 131 pages, 2010.

* cited by examiner

PROSTHETIC SUPPORT SOCKET FOR AN OSSEOINTEGRATED FEMORAL ABUTMENT

CROSS-REFERENCE TO RELATED PATENT APPLICATIONS

This application claims priority to U.S. Provisional Patent Application No. 62/197,427, entitled "Prosthetic Support Device for an Osseointegrated Femoral Abutment," filed Jul. 27, 2015; 62/267,820, entitled "Prosthetic Support device for an Osseointegrated Femoral Abutment," filed Dec. 15, 2015; and 62/364,930, entitled "Prosthetic Sockets that are Sensor Enabled to Provide Data for Clinical Use and Mechanical Adjustments," filed Jul. 21, 2016. The entireties of all the above-identified applications are hereby incorporated by reference for all purposes.

TECHNICAL FIELD

This application relates to medical devices and specifically prosthetic devices for amputated limbs. More specifically, the application relates to a prosthetic socket configured to support an osseointegrated abutment implanted in a residual limb and to protect the percutaneous site where the abutment emerges from the distal end of the residual limb.

INCORPORATION BY REFERENCE

All publications and patent applications identified in this specification are herein incorporated by reference to the same extent as if each such individual publication or patent application were specifically and individually indicated to be so incorporated by reference.

BACKGROUND

In the prosthetics field, osseointegration refers to orthopedic solutions to an amputation that involve a device that is integrated with the residual bone and extends linearly beyond the bone and through the skin for external engagement with a prosthetic device. Osseointegration is a well-established therapeutic approach in the context of dental implants. The jaw and oral environment are naturally suited to teeth emerging from bone, through the oral epithelium, and into the oral environment. Further, while teeth are exposed to considerable force, forces acting on teeth are generally vertical, and the teeth are well seated in bone and provide each other lateral support. In contrast, osseointegrated devices implanted in a long bone, such as a femur, pose a challenge, in that the percutaneous site through which the osseointegrated abutment emerges from within the limb to the external environment is not a naturally suited site for a percutaneous device. Additionally, although the forces to which the abutment is typically exposed come primarily from a direction linearly aligned with the abutment, an impacting force may come from any direction and may be very strong and unpredictable.

Osseointegration has become a potentially advantageous therapeutic option for transfemoral or knee disarticulation amputations, especially when a patient has not done well with conventional prosthetic sockets. Prosthetic sockets can be unsatisfactory or fail for patients for a number of reasons, but primarily because of comfort issues. Discomfort is not a trivial complaint for amputees with prosthetics. Sites of discomfort can cause serious skin ulceration and debilitating muscle or bone pain associated with the transfer of force through the residual limb. The theory underlying osseointegration is that by engaging the bone of the residual limb directly, and in an appropriate orientation, the need for a socket is eliminated (thus, eliminating socket-based problems) and the abutment provides a direct, biomechanically appropriate connection with a distal prosthetic element. From the patient perspective, an osseointegrated solution also offers the potential of a less cumbersome and less time consuming daily routine, compared to the use of prosthetic sockets and liners.

Osseointegrated metal abutments for residual limbs, however, have been found to have a number of vulnerabilities. First, the percutaneous site on the residual limb is vulnerable to irritation and infection, even after the site heals following implantation of an osseointegrated abutment. Second, the distally exposed metal abutment is called upon to absorb a considerable level of force (and an associated moment of force) that the host bone needs to absorb. Accordingly, the host bone may be subject to erosion and, in the worst case, fracturing and disintegrating.

Therefore, it would be beneficial to have improved osseointegration devices, which would address at least some of the vulnerabilities described above. The embodiments described below will address at least some of these vulnerabilities.

SUMMARY

Embodiments of the invention are directed to an osseointegrated abutment support socket for a residual limb in which an osseointegrated abutment has been implanted, such implanted abutment having a distal end projecting distally beyond the host residual limb through a percutaneous site in the residual limb. In addition to structural aspects of the osseointegrated abutment support socket, embodiments of the invention are directed to methods of coupling an implanted osseointegrated abutment to an osseointegrated abutment support socket.

Embodiments of the invention include a distal socket base assembly, that assembly having a base plate, a collar extending proximally from the base plate and forming a receptacle for receiving a distal end of the osseointegrated abutment, and a strut support ring disposed around the collar. The invention further includes a longitudinal portion that has multiple longitudinal struts connected at their distal ends to the strut support ring, the longitudinal struts extending proximally upward from the strut support ring. Embodiments of the invention may optionally further include a percutaneous site protector coupled with at least one of the distal socket base assembly or the longitudinal struts, the percutaneous site protector configured to contact a distal surface of the residual limb around or near a percutaneous site where the distal end of the osseointegrated abutment exits the residual limb.

In some embodiments of the osseointegrated abutment support socket, the multiple longitudinal struts comprise a thermoplastic fiber composite material. For example, in some embodiments, the multiple longitudinal struts consist entirely of a thermoplastic fiber composite material. U.S. patent application Ser. No. 14/213,788, filed on Mar. 14, 2015 (U.S. Published App. No. 2014/0277584), describes such a composition and methods for forming struts to provide an optimal fit.

In some embodiments of the osseointegrated abutment support socket, the percutaneous site protector is configured to form a seal with the residual limb around the percutaneous site. Some embodiments of the osseointegrated abutment support socket further include a support cup disposed proximate an inner surface of the longitudinal struts, within a cavity formed by the longitudinal struts, and proximal to the distal socket base assembly; the percutaneous site protector is disposed on or supported by this support cup. In particular embodiments, the abutment percutaneous site protector includes a proximal dressing layer that includes or is impregnated by at least one of an antimicrobial agent or a bioactive agent.

Some embodiments of osseointegrated abutment support socket of claim further include at least one tensioning band disposed circumferentially around the longitudinal struts (typically disposed closer to proximal ends of the longitudinal struts than to their distal ends), and a tension adjustment mechanism operatively connected to the at least one tensioning band. In particular embodiments, the tensioning band is disposed circumferentially around all multiple struts. When tensioned, the tensioning band draws the multiple longitudinal strut are closer together, and by so doing, increases a level of compression on a host residual limb hosted within the osseointegrated abutment support socket.

In some embodiments of the osseointegrated abutment support socket, the osseointegrated abutment has a distal knob. The distal knob and an internal surface of the receptacle of the collar collectively form a complementary quick release feature whereby the osseointegrated abutment support socket may be releasably secured around the distal knob. In particular embodiments and by way of example, the quick release feature may include a groove around the distal knob of the abutment, and an internal surface of the receptacle of the collar may include a ball bearing.

In some embodiments of the osseointegrated abutment support socket, the strut support ring has multiple buttressed strut connectors configured to connect the longitudinal struts to the strut support ring. The buttressed strut connectors are disposed on a distal aspect of the strut support ring, increasing the level of support provided to the multiple longitudinal struts.

In some embodiments of the osseointegrated abutment support socket, at least one of the strut connectors has a directionally biased hinge mechanism. More particularly, the directionally biased hinge mechanism may be configured to freely allow inward deflection of the longitudinal struts from a distal attachment site and outward deflection of the longitudinal struts by way of a release mechanism.

Some embodiments of osseointegrated abutment support socket may further include an evacuation chamber in the base plate of the distal socket base assembly. Such embodiments may further include a vacuum line fluidly connected with the evacuation chamber at one end and an opening in a proximal surface of the percutaneous site protector at an opposite end, the opening providing a distal escape for fluid that may accumulate within the distal cavity of the osseointegrated abutment support socket. Some embodiments of the evacuation chamber may be compressible; such compressibility may enable a pumping mechanism that actively draws fluid through the vacuum line; such compressibility may further serve a shock absorbing function.

Some embodiments of osseointegrated abutment support socket may further include at least one sensor coupled with the support socket and configured to sense at least one of a load or torsion transferred from the residual limb to a portion of the abutment support socket. In particular embodiments, the at least one sensor is selected from the group consisting of a load sensor and a torsion sensor disposed within the socket, the sensor including a transmitter configured to transmit sensed data. Sensors disposed within the osseointegrated abutment support socket may further be configured to sense any of acceleration and position. Sensors may be positioned at any suitable or effectively informative location within the osseointegrated abutment support socket, as by way of example, the percutaneous site protector, any of the longitudinal struts, or on or within the distal socket base assembly.

As noted above, embodiments of the invention also include methods for coupling a residual limb in which an osseointegrated abutment has been implanted with an osseointegrated abutment support socket (may be referred to as a "coupling method"). Such coupling methods include advancing a distal end of the residual limb into an open proximal end of the osseointegrated abutment support socket, the open proximal end being formed by multiple longitudinal struts typically encircled by or coupled together with a tensioning band. Embodiments of the coupling method further include advancing the residual limb further into the osseointegrated abutment support socket to cause a distal end of the osseointegrated abutment to pass into and lock with a receptacle within a distal socket base assembly of the osseointegrated abutment support socket. Embodiments of the coupling method further include contacting the distal end of the residual limb with a percutaneous site protector of the osseointegrated abutment support socket, wherein the percutaneous site protector forms a seal with the distal end of the residual limb near or around a percutaneous site where the distal end of the osseointegrated abutment exits the residual limb.

Some embodiments of the coupling method include evacuating fluid from a space between the distal end of the residual limb and the percutaneous site protector, using a vacuum line fluidly connecting the space with an evacuation chamber in the distal socket base assembly.

Some embodiments of the coupling method include adjusting tension in the tensioning band by using a tension adjusting mechanism attached to the tensioning band. In some of these embodiments, adjusting the tensioning band includes adjusting a level of compression applied around the multiple longitudinal struts to adjust a fit of the osseointegrated support abutment on a hosted residual limb.

Some embodiments of the coupling method further include preventing infections or supporting healing in the percutaneous site by providing the percutaneous site protector with at least one of an antimicrobial agent or a bioactive agent.

Some embodiments of the coupling method further include removing the osseointegrated abutment support socket from the residual limb by releasing a quick release mechanism that releasably attaches the distal end of the osseointegrated abutment to the receptacle.

Some embodiments of the coupling method further include sensing a force of the residual limb on the osseointegrated abutment support socket, such sensing mediated by using at least one sensor coupled with the osseointegrated abutment support socket. In particular embodiments, the at least one sensor is coupled to any one or more of a sites on at least one of the multiple struts, the percutaneous site protector, or the distal base assembly. In particular embodiments, sensing the force includes sensing at least one of load and torsion. In other embodiments, at least one sensor may be configured to sense acceleration or position. Some embodiments of these sensor-enabled methods may further include transmitting data related to the sensed force, using a transmitter coupled with or supported by the osseointegrated abutment support socket.

Some embodiments of the method further include attaching a distal prosthetic component to the osseointegrated abutment support socket via the distal socket base assembly. In particular embodiments, the distal prosthetic component comprises using a four-hole adapter on a distal surface of the distal socket base assembly to connect to the distal prosthetic component.

DETAILED DESCRIPTION OF THE INVENTION

Figure 1:
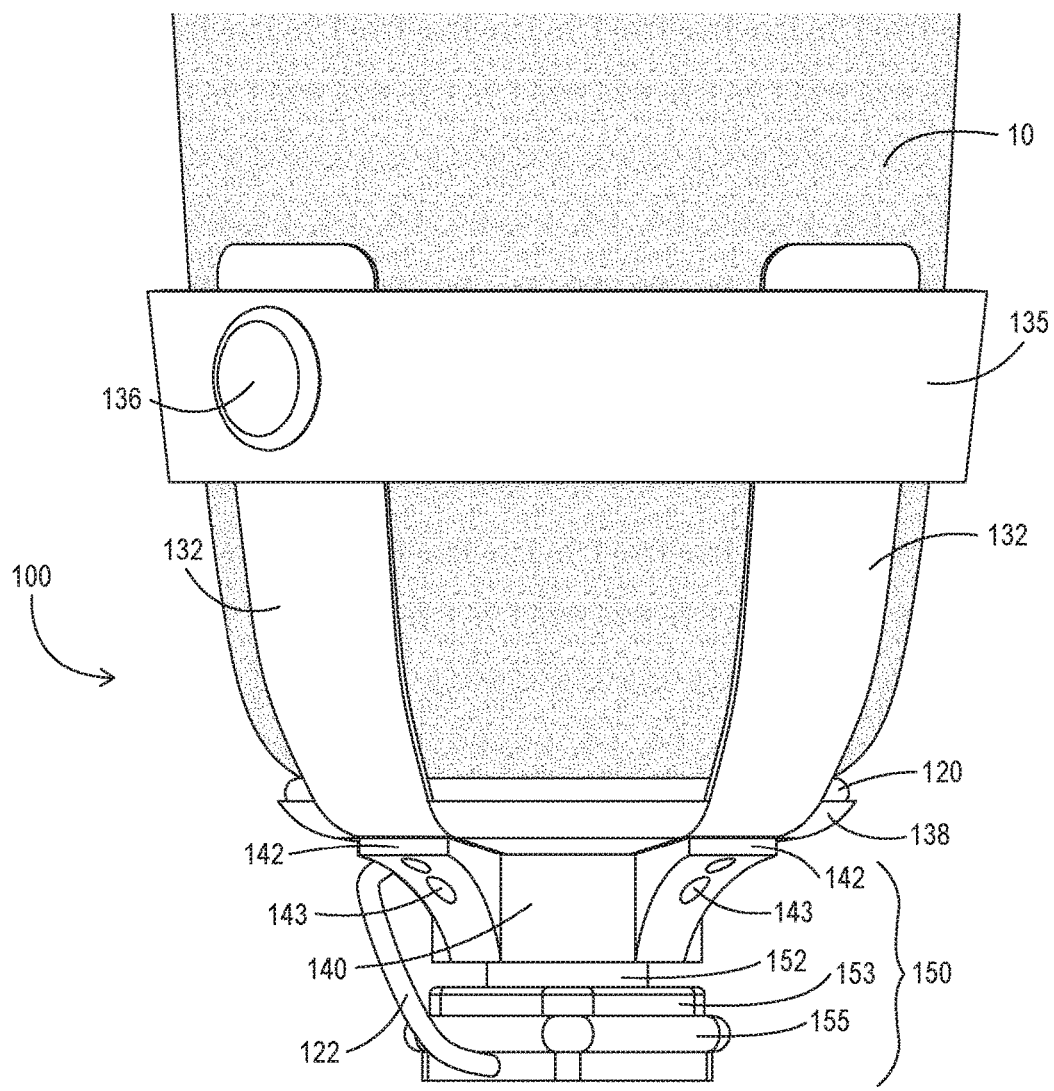
FIG. 1 is a side view of an osseointegrated abutment support socket in one embodiment, the socket hosting the residual thigh of a patient, the socket including an abutment percutaneous site protector.

As summarized above and illustrated in FIGS. 1-16, basic elements of embodiments of an osseointegrated abutment support (hereinafter abbreviated as "OIAS") socket 100 include a longitudinal portion comprising multiple longitudinal struts 132, one or more tensioning bands 135 encircling the struts 132, a percutaneous site protector 120, and a distal socket base assembly 150.

Figure 2:
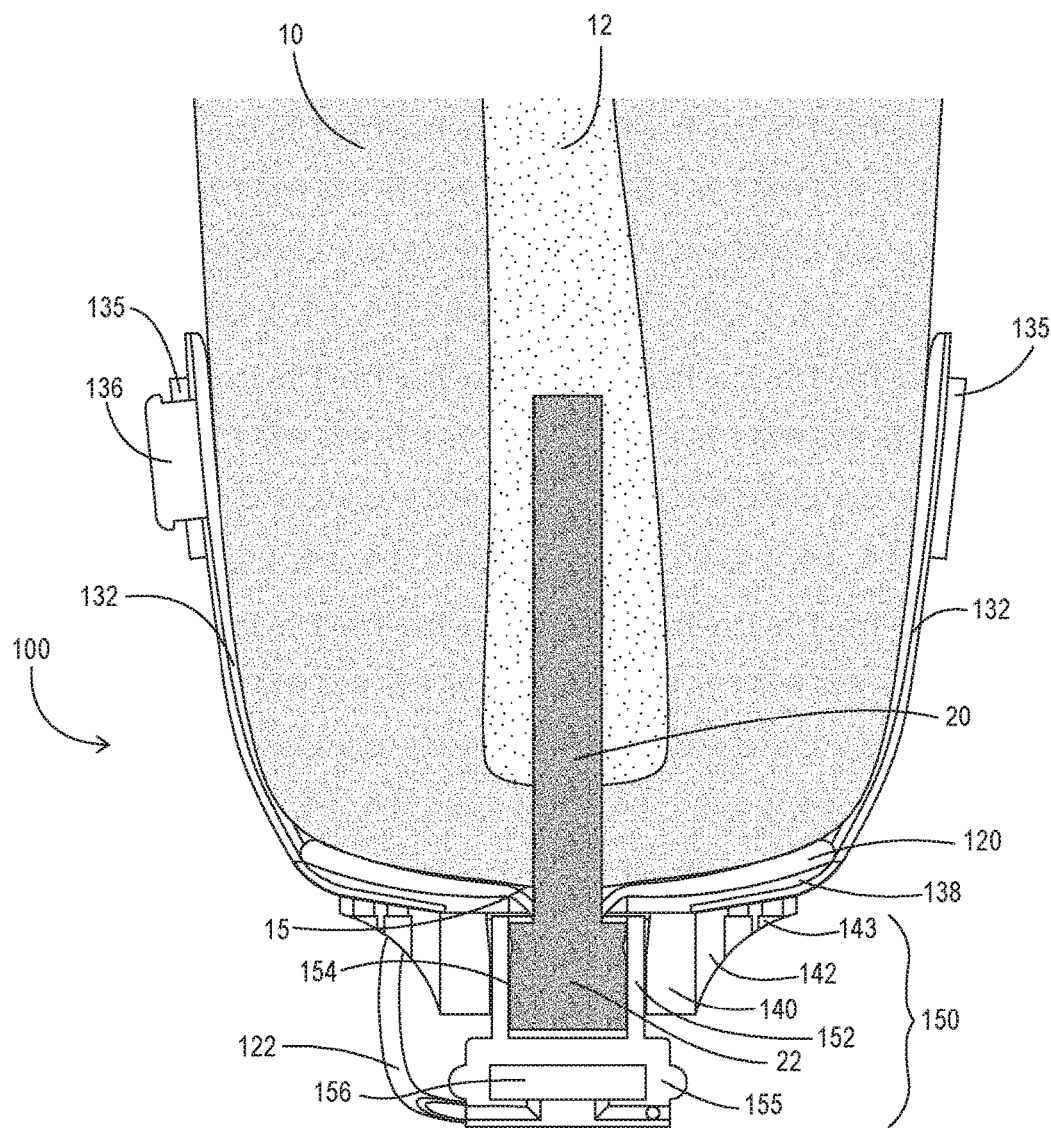
FIG. 2 is a side cross sectional view of an osseointegrated abutment support socket in one embodiment, the socket hosting the residual thigh of a patient, the femur of the patient shown with the osseointegrated abutment inserted thereinto.

Referring to FIG. 2, OIAS socket 100 is configured to host a residual limb, such as a residual thigh 10, having a residual long bone such as femur 12. An osseointegrated abutment 20 is shown implanted in femur 12, and projecting distally therefrom. The proximal end of osseointegrated abutment 20 is embedded in femur 12; the distal portion projects distally through a percutaneous emergent site 15 in residual limb 10. The distal end of osseointegrated abutment 20 includes a knob 22 that may have a quick release feature 24 (FIG. 6) that engages a mating feature within distal socket base assembly 150, as described further below.

OIAS socket 100 may further include an internal space 156 within distal base assembly 150 that, in various embodiments, may serve as an evacuation chamber that draws fluid in from the space proximate the percutaneous abutment emergent site and the percutaneous site protector 120, a reservoir for such fluid, as well as a shock absorber that dampens impact of the patients stride. These elements of OIAS socket 100, as well as alternative embodiments, are described in further detail below.

OIAS sockets, as described herein, are appropriate for a residual limb of an above-the-knee amputation or transfemoral amputation. This is but one non-limiting example of an amputation site that can be fitted with such an osseointegrated abutment. Other examples include trans-tibial sites in the leg, and trans-humeral and trans-radial sites of amputation in the arm.

It takes between six months and a year for an osseointegrated (or "osseointegratable") abutment and the host bone site to become optimally integrated. In one aspect of their use, OIAS sockets are particularly important during this initial year following abutment insertion, as they serve to protect the abutment from excessive load bearing or torque that could injure the host bone or disrupt osseointegration. In some approaches, the use of an osseointegrated support sockets may be discontinued after it has been determined that the abutment is secure and well integrated into the host bone.

In other approaches, a patient may continue to use an osseointegrated support socket, even after an abutment is determined to be secure. In some instances, this may simply be the preference of the patient or, alternatively, it may be determined by an orthopedist that it would be beneficial to continue to use the support socket for a period of time. In some approaches, a patient may partially discontinue use of an OIAS socket in general, but make use of it on particular occasions, such as when the patient is engaging in physical activity that is particularly demanding.

In some embodiments, components of OIAS socket 100 may be modular in character. By way of example, multiple struts 132, strut support ring 140, distal socket base assembly 150, and/or an abutment percutaneous site protector 120 may be drawn from an inventory of such components, including a collection of such components that vary by size and/or shape but are nevertheless connectable by common connecting features. In typical embodiments, modular components may be easily removed from an assembled OIAS socket and a new component put in place, the new component having substantially the same size and shape of the replaced component, or varying in any of the aspects.

In some embodiments, the abutment percutaneous site protector 120 may be drawn from an inventory of site protector components that are configured to be easily replaced and are fabricated in a manner appropriate for disposable components.

The longitudinal portion of an OIAS socket, as described and depicted herein, typically includes four longitudinal struts formed from a thermoplastic fiber composite material. Alternative embodiments may include fewer or more than four such struts. Alternative embodiments may include struts formed from other suitable materials. Alternative embodiments need not include struts at all, but instead may be shaped as a more enclosed structure, such as seen in conventional laminated thermoset plastic prosthetic sockets. Such alternative sockets may include windows or movable portions that provide size or shape adjustments.

FIGS. 1 and 2 show, respectively, a side view and a side cross-sectional view of OIAS socket 100 according to one embodiment, the socket 100 hosting the residual thigh 10 of a patient who has had a transfemoral amputation and an osseointegrated abutment 20 implanted into the distal end of the residual femur 12. The distal end of osseointegrated abutment 20, which extends distally beyond the residual limb, protrudes through a percutaneous emergent site 15 in the residual limb. A knob 20 is disposed at the distal end of osseointegrated abutment 20. When residual limb 10 is being hosted by OIAS socket 100, knob 20 is held securely within a receptacle 154 of the collar portion 152 of distal base assembly 150; collar portion 152, itself, is securely held within a central hole of strut support ring 140.

OIAS socket 100 includes multiple longitudinal struts 132 (sometimes one or more tensioning bands 135 encircling the struts 132, a percutaneous site protector 120, and a distal socket base assembly 150 that includes strut support ring 140. In some embodiments, OIAS socket 100 includes four longitudinal struts 132, although alternative embodiments may have fewer or more struts 132. A tensioning band 135 typically includes a tension mechanism 136 that may be configured as a low profile Boa-style crank tensioner. Strut support ring 140 includes distally disposed buttress elements 142, which may also serve as strut connecting sites with strut connecting holes 143 for attachment of longitudinal struts 132 on the proximal surface of the strut support ring 140.

Strut support ring 140 forms a distally open well that fits over distal socket support base 150, more particularly, fitting over collar portion 152 of distal socket base assembly 150. Collar portion 152 is raised proximally above a base plate 153. Optionally, base plate 153 may include an evacuation chamber 156 (see FIG. 2), can serve as a reservoir for fluid drained from the percutaneous abutment emergent site.

When OIAS socket 100 is fully assembled, a plastic support cup 138 (referring to support for percutaneous site protector 120) is disposed within socket 100 at its distal end, where it is supported by socket base ring 140. Support cup 138, in turn, supports proximally disposed abutment percutaneous site protector 120, which is applied against the distal end of residual thigh 10 over percutaneous abutment emergent site 15. Percutaneous site protector 120 is configured to be evacuatable by a negative pressure draw through vacuum line 122.

Figure 3:
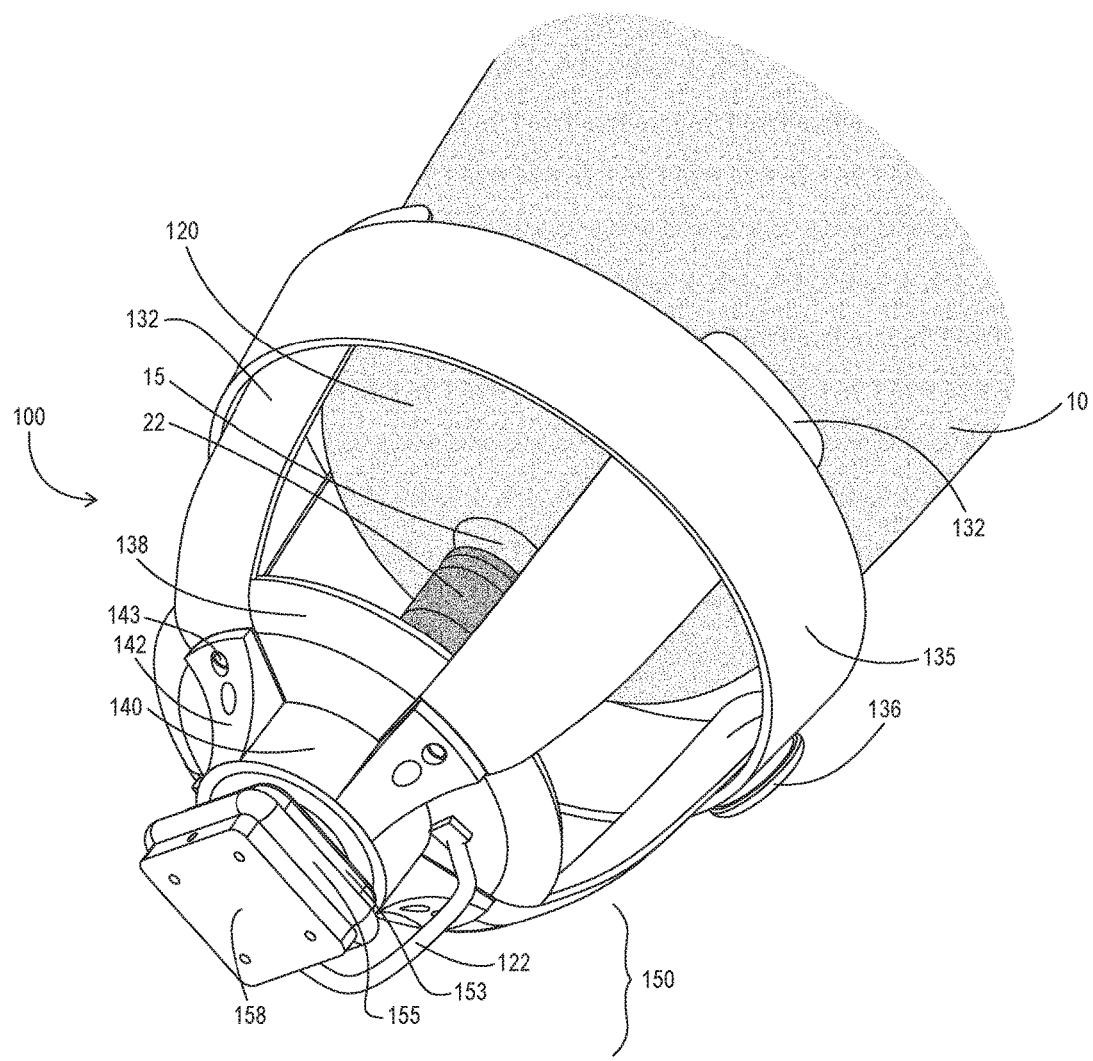
FIG. 3 is a bottom perspective view of an osseointegrated abutment support socket in one embodiment, the socket hosting the residual thigh of a patient.

FIG. 3 shows a bottom perspective view of an OIAS socket in one embodiment, the socket hosting the residual thigh of a patient. In this particular view, the residual thigh 10 of the patient is not fully inserted into the distal well of OIAS socket 100. Abutment knob 22 is seen emerging from percutaneous abutment emerging site from residual thigh 10. Vacuum line 122 is seen extending from the distal surface of percutaneous site cup protector 138, and entering distal base assembly 150 where it empties into an evacuation chamber 156 that also serves as a drainage fluid reservoir (FIG. 2). This particular embodiment of distal base assembly 150 is connected distally to a 4-hole adapter 158 that can connect to distal prosthetic elements (not shown).

Figure 4:
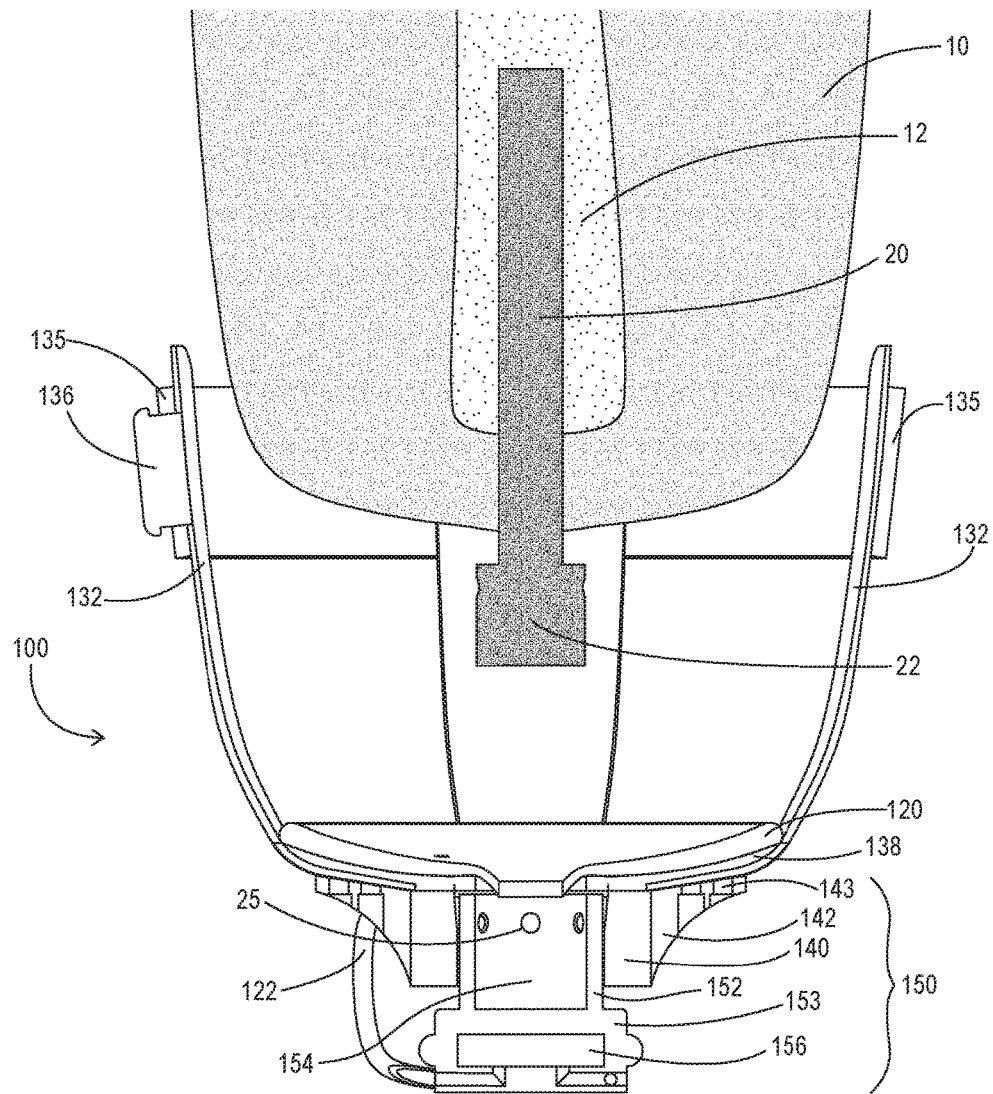
FIG. 4 is a cross sectional view of the residual thigh of a patient with an abutment implanted into the femur and an osseointegrated abutment support socket, in one embodiment, the distal end of the abutment and the abutment support socket lined up with each other but not engaged.

FIG. 4 shows a cross sectional view of the residual thigh 10 of a patient with an abutment 20 implanted into the femur 12. As in FIG. 3, the residual thigh 10 of the patient is not fully inserted into the distal well of OIAS socket 100. Collar 152 defines a receptacle 154 that is configured to accommodate the distal knob portion 22 of abutment 20.

Figure 5:
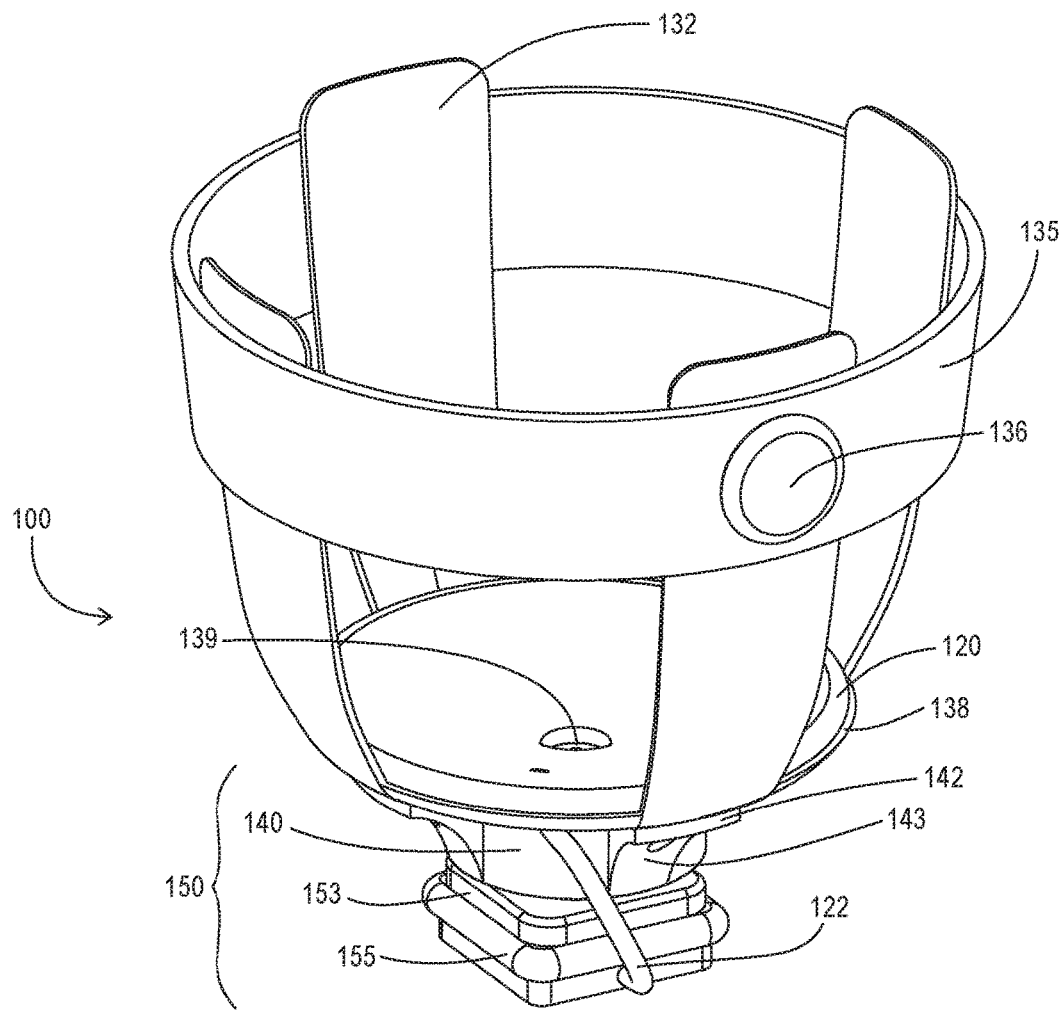
FIG. 5 is a top perspective view of an osseointegrated abutment support socket in one embodiment, showing in particular the proximal surface of a percutaneous site protector, the site protector disposed within the distal cavity defined by the socket.
Figure 12:
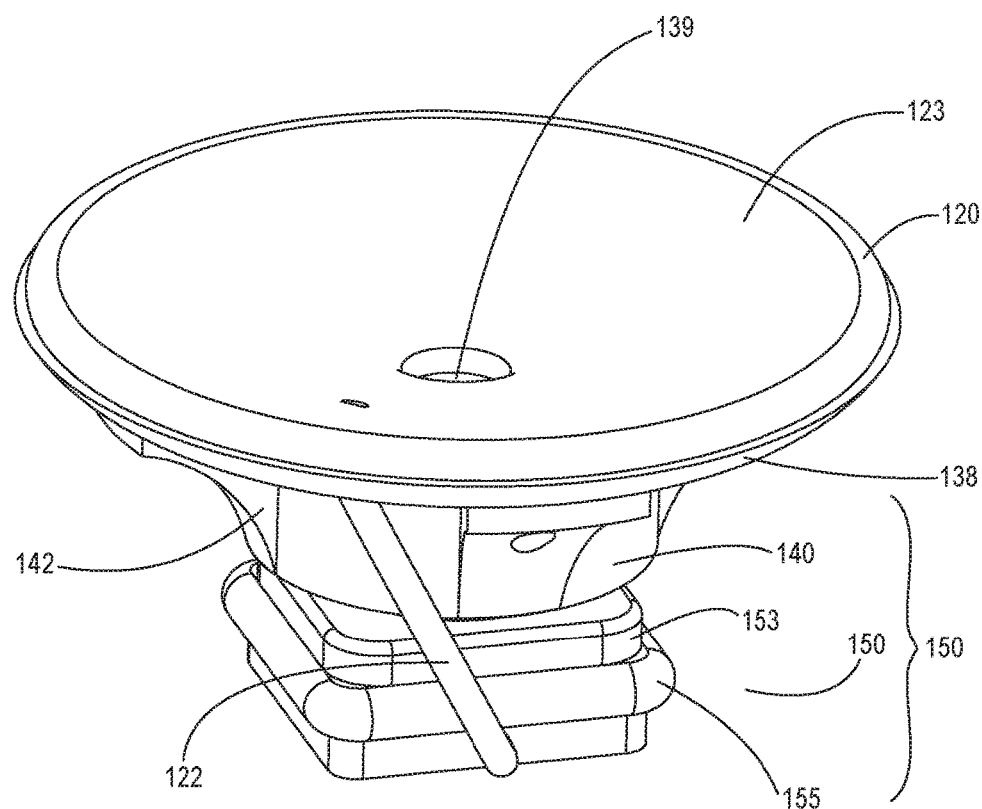
FIG. 12 is a top perspective view of a central portion of an osseointegrated abutment support socket, showing, in particular, a dressing layer disposed over a percutaneous site protector support cup, the dressing layer providing a substrate for antimicrobial compounds and/or bioactive agents.

FIG. 5 shows a top perspective view of an OIAS socket 100 in one embodiment, showing in particular the proximal surface of a percutaneous site protector 120, as it is disposed within the distal cavity defined by OIAS socket 100. A central hole 139, for accommodating a distal end of an osseointegrated abutment (not shown) penetrates through percutaneous site protector 120, and percutaneous site protector support cup 138. As shown in FIG. 12, the upper surface of percutaneous site protector 120 may be impregnated with medicinal agents that prevent or combat infection, or which aid in wound healing.

In some embodiments, draining fluid from around a residual limb's percutaneous site 15 may be facilitated by a vacuum draw into a fluid reservoir. The reservoir may include an expandable air space that can be compressed as the patient walks, this action may be also exploited as a shock absorbing function.

Some embodiments of the OIAS socket 100 may have UV light emitting diodes disposed within or proximate the percutaneous site protector to perform an anti-infective function. And some embodiments of the OIAS socket include devices to monitor the structural integrity of the abutment or bone of the residual limb by way of sonic, electrical, or magnetic testing methods.

FIGS. 6-9 all ¾ sectional views that focus on aspects of a central mechanism by which OIAS socket 100 and elements of distal base assembly 150, in particular, securely engage abutment 20 and its distal knob 22, in particular. This is a reversible engagement, enabled by quick release features disposed within distal base assembly 150 and the exterior surface of distal knob 22.

Figure 6:
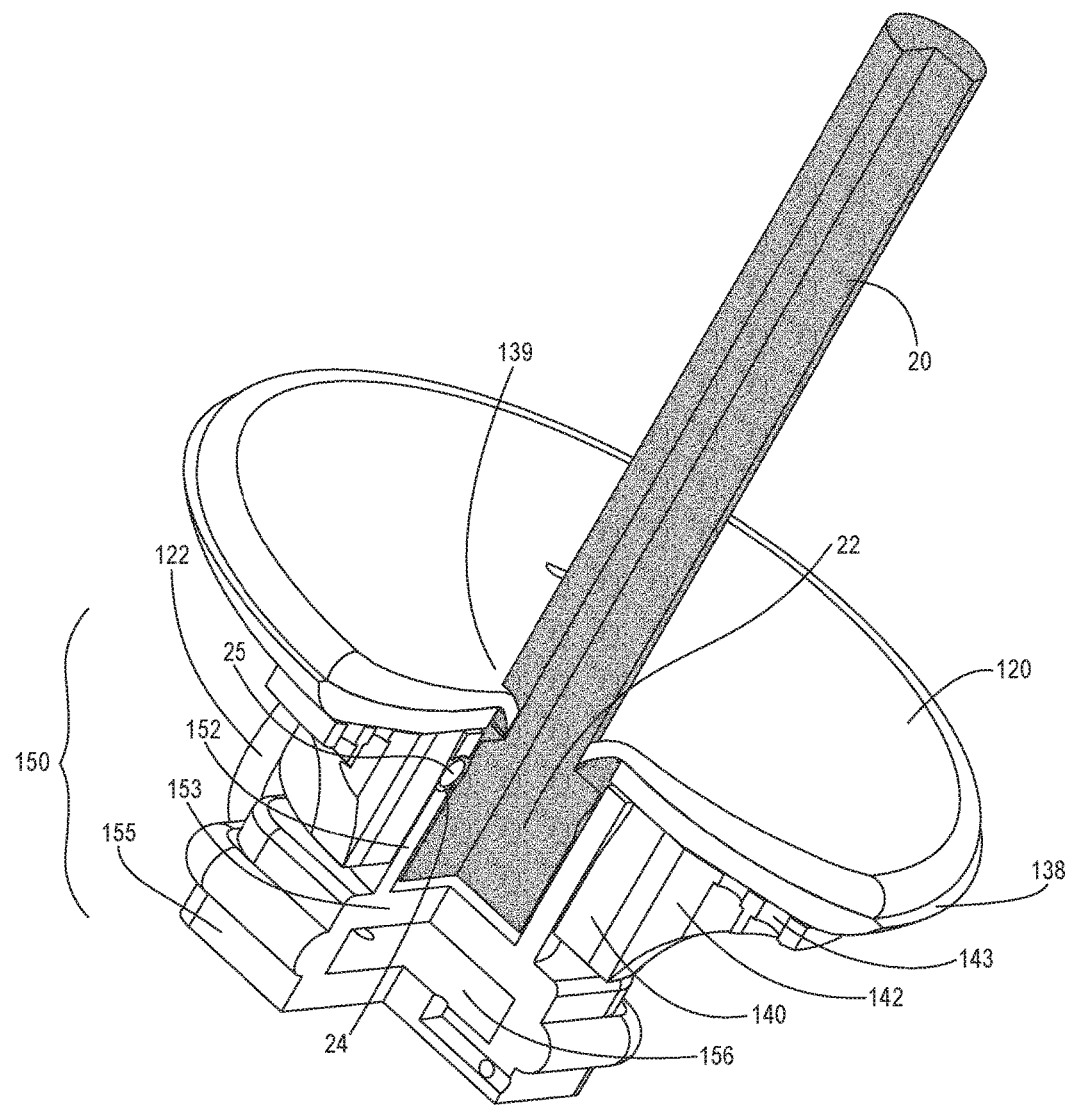
FIG. 6 is a top perspective ¾ sectional view of the distal end of an abutment secured within a distal base assembly, the distal end of the abutment secured within a collar portion of a distal base assembly.
Figure 7:
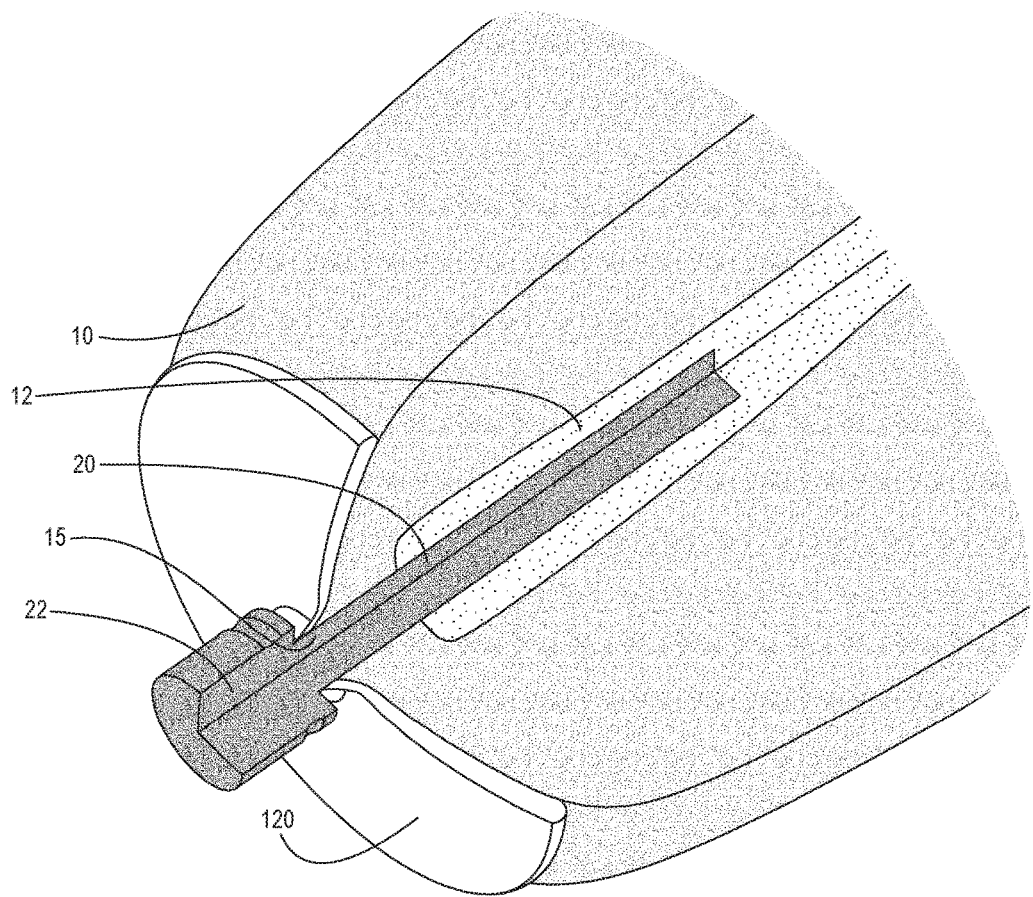
FIG. 7 is a bottom perspective ¾ sectional view of the residual thigh of a patient with an abutment emergent site sealing unit applied to the distal end of the residual thigh, covering the percutaneous abutment emergent site in the residual thigh.

FIG. 6 shows a top perspective ¾ sectional view of the distal end 22 of an abutment 20 secured within collar portion 152 or distal socket support base 150, while the collar portion 152, itself, is secured within strut support base 140. Struts 132 are not shown in this view. FIG. 7 is an upward-looking view uncomplicated by OIAS socket components. It provides bottom perspective ¾ sectional view of the residual thigh 10 of a patient with an abutment emergent site sealing unit 120 applied to the distal end of the residual thigh, covering the percutaneous abutment emergent site 15. Neither longitudinal struts 132 nor distal socket support base 150 are shown in this view.

Figure 8:
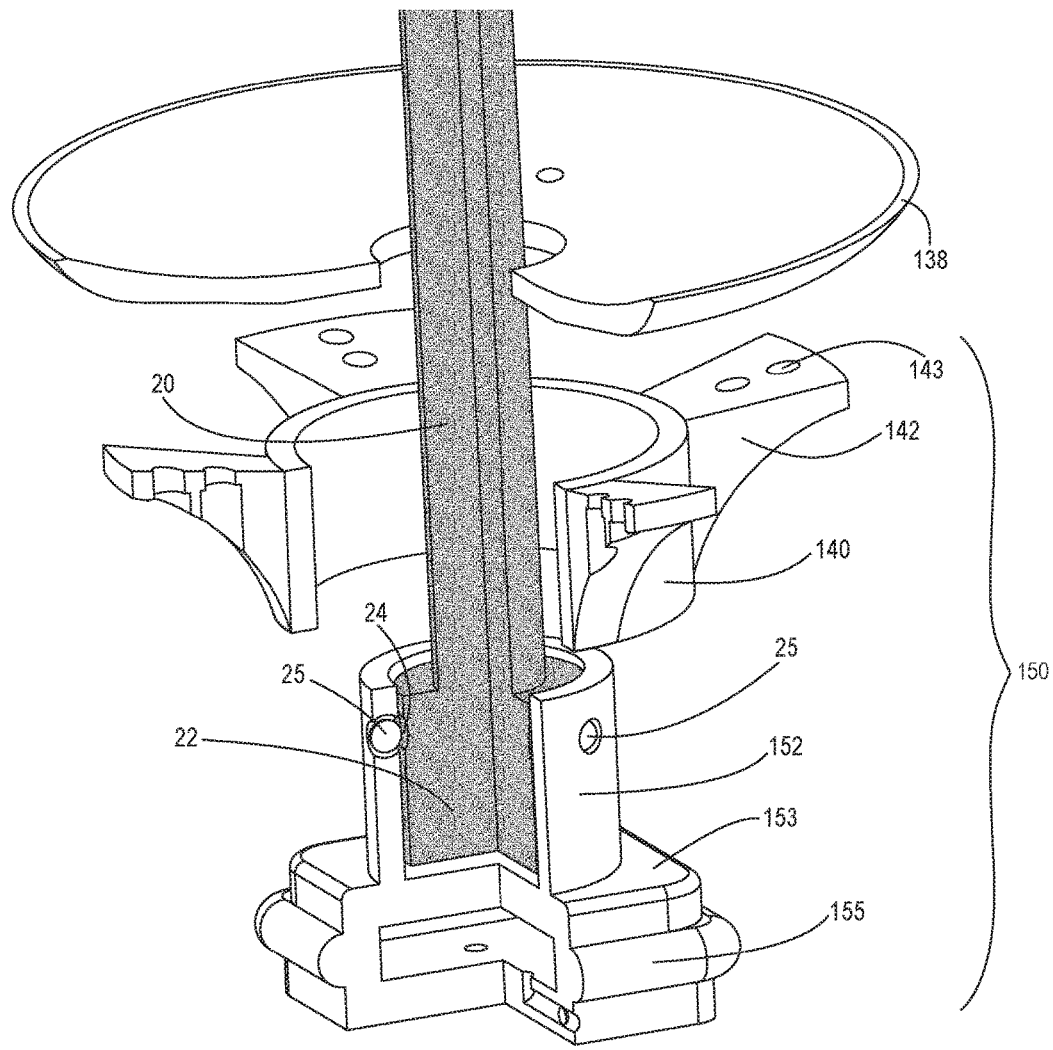
FIG. 8 is a partially-exploded top perspective ¾ sectional view of a portion of an osseointegrated abutment support socket in one embodiment, showing in particular the distal support base of the socket (embracing the distal knob of the abutment), a strut support ring, and a percutaneous site protector.
Figure 9:
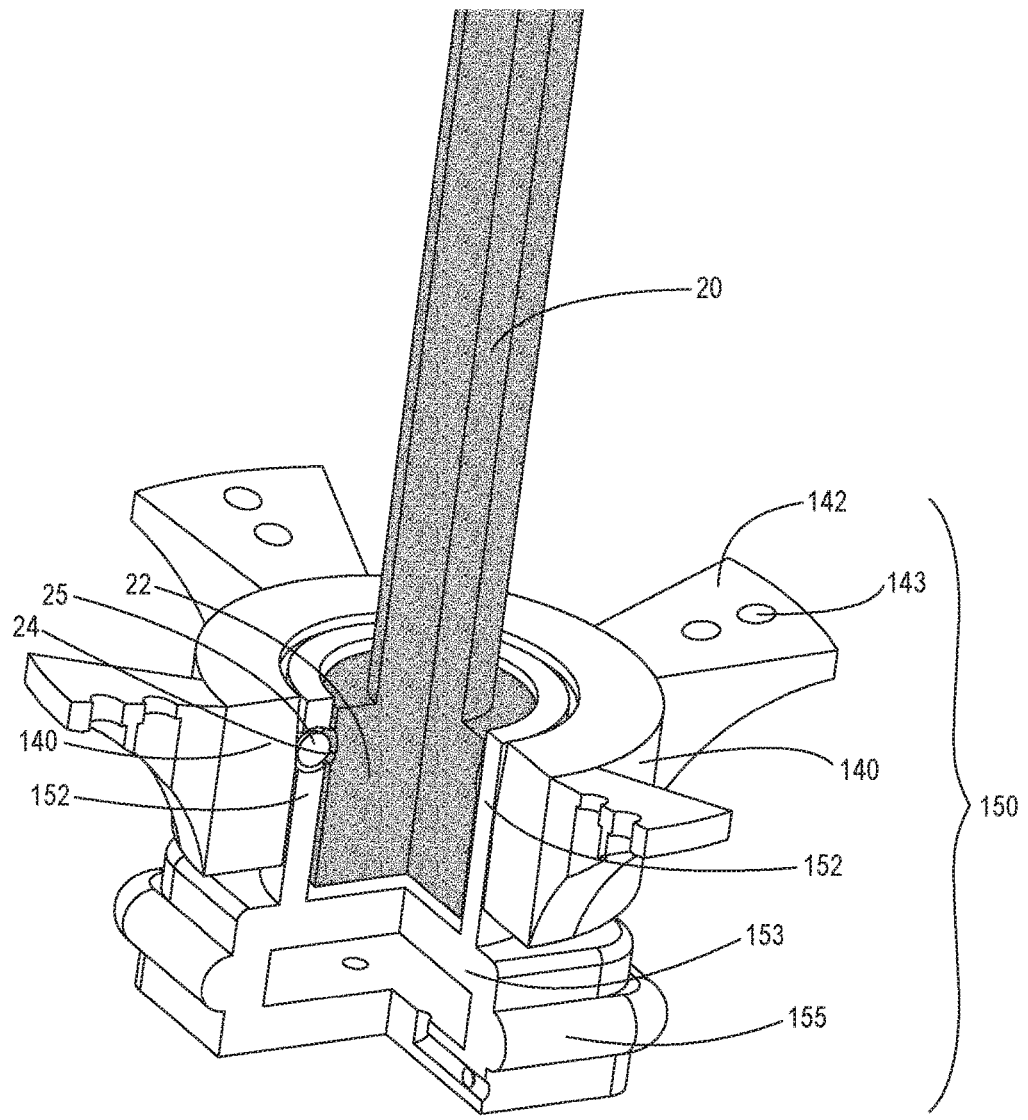
FIG. 9 is a top perspective ¾ sectional view of a portion of an osseointegrated abutment support socket, in one embodiment, showing in particular the distal end of the abutment disposed within a distal base of the socket, the distal base disposed with a collar portion of the socket.

FIG. 8 shows a vertically-exploded top perspective ¾ sectional view of a portion of an OIAS socket 100 in one embodiment, showing in particular the distal support base 150 of the socket (embracing the distal knob of 22 the abutment 20), the strut support ring 140, and support cup 138 for the percutaneous site protector (not shown). FIG. 9 shows the same set of components as in FIG. 8 (except for percutaneous site protector support cup 138) arranged into an assembled form. It provides a top perspective ¾ sectional view of a portion of an OIAS socket 100, in one embodiment, showing in particular the distal end 22 of abutment 20 disposed within a strut support base 150, which, itself, is disposed with a collar portion 152 of distal socket support base 150. Struts 132 are not shown in this view.

FIGS. 8 and 9 show complementary or mutually engageable quick release features 24 and 25. Release feature 24 is on an external surface of the distal knob 22 of abutment 10, and in one embodiment is a circumferential groove around the distal knob. Release feature 25 is disposed on the interior aspect of collar portion 152 or distal socket support base 150, and in one embodiment is a ball bearing hosted in a receptacle. This is merely one example of a suitable quick release mechanism that can serve to secure abutment 20 within distal socket support base 150.

Figure 10:
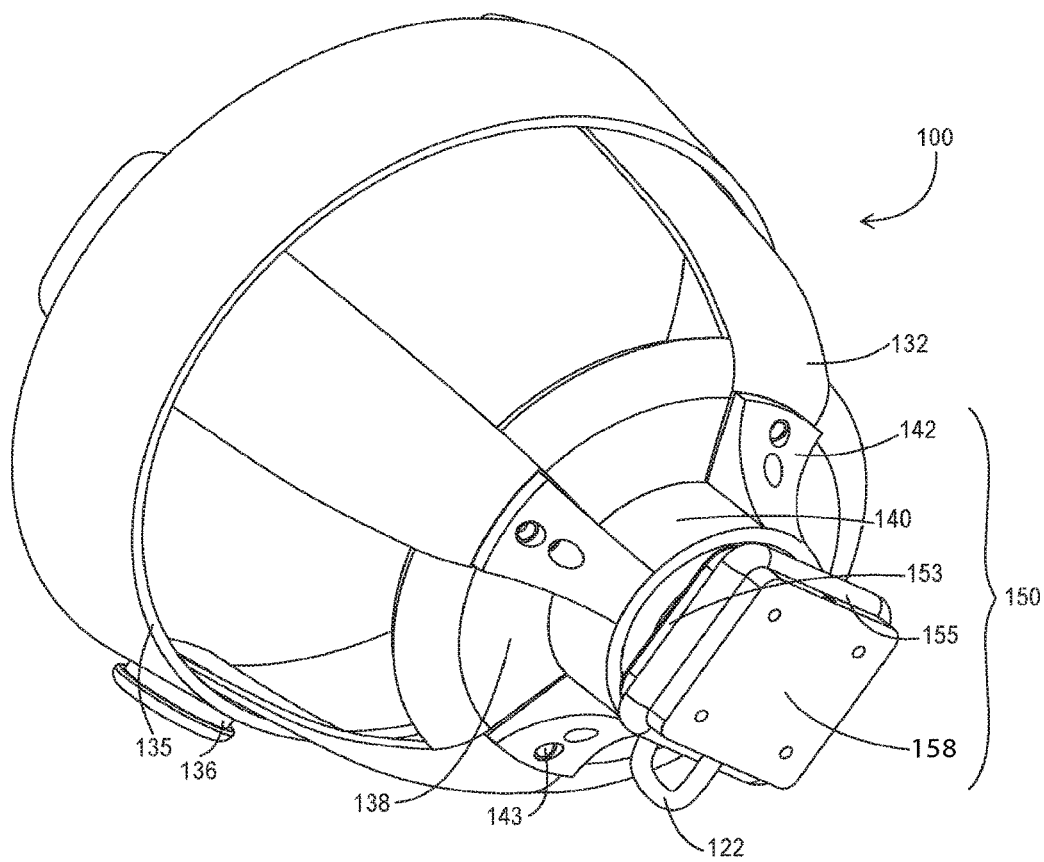
FIG. 10 is a bottom perspective view of an osseointegrated abutment support socket in one embodiment, showing in particular a 4-hole adaptor plate affixed to the distal end of the socket, the 4-hole adaptor configured to connect to a distal prosthetic element such as a knee or pylon.

FIG. 10 shows a bottom perspective view of an OIAS socket 100 in one embodiment, showing in particular a 4-hole adaptor plate 158 affixed to the distal end of the distal socket support base 150. A 4-hole adaptor 158 is an example of one among several standard component of prosthetic sockets that is configured to be able to connect to a distal prosthetic element such as a knee or pylon (not shown).

Figure 11:
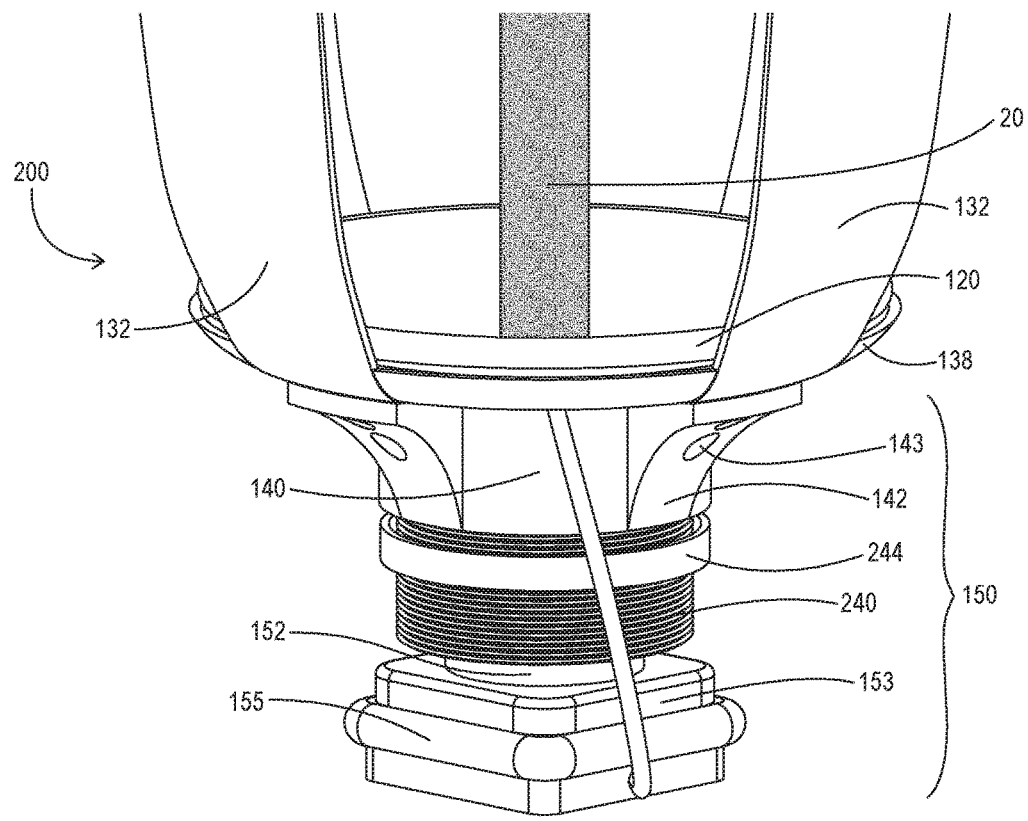
FIG. 11 is a top perspective view of an osseointegrated abutment support socket, the socket featuring a lengthened and threaded embodiment of a base support ring and distal base insert.

FIG. 11 shows a top perspective of an OIAS socket 100, the socket featuring an alternative distal support base embodiment 200 having a threaded collar portion 152. The length of an exposed distal end of an abutment beyond the skin surface of a residual limb in not necessarily standardized, and can thus vary. The functionality of this alternative distal base with a threaded locking collar is that it can accommodate abutments that extend beyond the percutaneous site of emergence of varying length.

FIG. 12 is a top perspective view of a central portion of an OIAS socket 100, showing, in particular, a wound dressing layer 123 disposed over a percutaneous site protector support cup 138, the dressing layer being a host substrate for antimicrobial compounds or suitable and beneficial medicinal agents. Dressing layer 123 may be integral or fused with underlying percutaneous support cup 138, or it may be a separate layer. In some embodiments, dressing layer may be designed as a disposable element. As noted above, the percutaneous site in the residual limb where an implanted osseointegrated abutment emerges can be vulnerable to infection and chronic inflammation. Thus, benefit may be derived from local application of medication as well as anti-infective measures; additionally, in some embodiments a UV light may be provided within the vicinity of wound dressing layer 123.

Figure 13A:
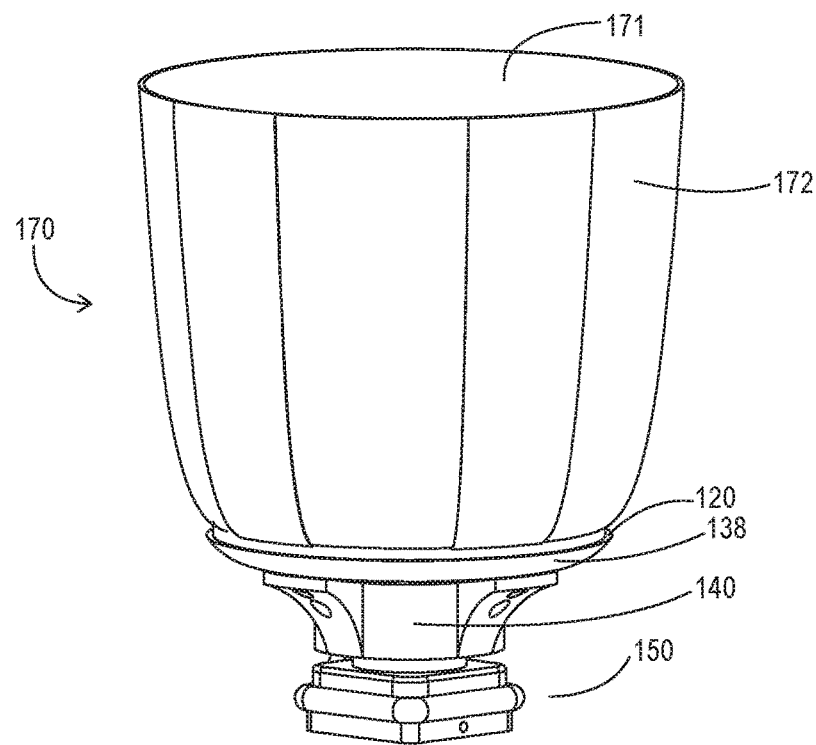
FIG. 13A is a top perspective view of a central portion of an osseointegrated abutment support socket with a roll-on liner garment disposed above a percutaneous site protector support cup.
Figure 13B:
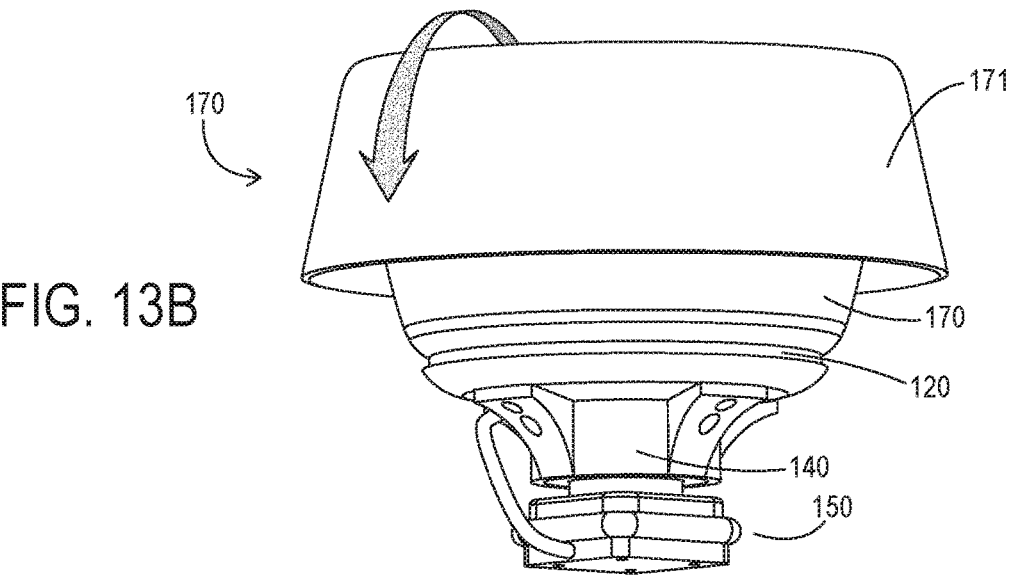
FIG. 13B is a top perspective view of a central portion of an osseointegrated abutment support socket with a roll-on liner garment disposed above a percutaneous site protector support cup as in FIG. 13A, showing the liner garment reflected back on itself as it would be for positioning it on a residual limb.

FIG. 13A is a top perspective view of a central portion of an OIAS socket 100 with a roll-on liner garment 170 disposed above a percutaneous site protector support cup 138. Roll-on liner garment 170 has an internal surface 171 and an external surface 172. FIG. 13B is a top perspective view of a central portion of an OIAS socket 100 with a roll-on liner garment 170 as in FIG. 13A with the liner garment reflected back on itself (as indicated by an arrow) for positioning it on a residual limb. These figures demonstrate the compatibility of OIAS socket 100 with conventional roll-on liners.

In some alternative embodiments, a percutaneous site protector 120 may be incorporated into a prosthetic socket roll on liner, such as that described in U.S. patent applicant Ser. No. 15/157,894 of Hurley et al., entitled "Prosthetic socket liner garment with a breathable proximal portion", as filed on May 18, 2016, which is incorporated into the present application by this reference. Such liner embodiments are reflectable, i.e., the liner can be donned by a conventional donning method that includes eversion or reflection of the liner, placing of the osseointegrated abutment through a central hole, and rolling the liner up and around the proximal portion of the residual limb (FIGS. 13A-13B). Prosthetic socket liner embodiments such as those described in the referenced provisional patent applications have breathable surface portions and include a wicking substrate for moisture escape.

FIGS. 14A-14D depict aspects of a strut 132 with a strut connector embodiment 133 having a variable position hinge mechanism that is included in some embodiments of OIAS socket 100. Other longitudinal struts (shown in a cut-off depiction to clarify the view) have a fixed position strut connecter 134. In typical embodiments of OIAS socket 100, only one of the total of four strut connectors includes this variable position hinge 133, and typically the hinged strut connector is disposed at a lateral position, particularly an anterior lateral position. In some embodiments two or more of the four strut connectors may be configured with a variable position hinge. The function of this variable position hinge is to allow a quick donning of the OIAS socket by opening (externally deflecting) the strut to allow the user to easily step into the socket.

Figure 14A:
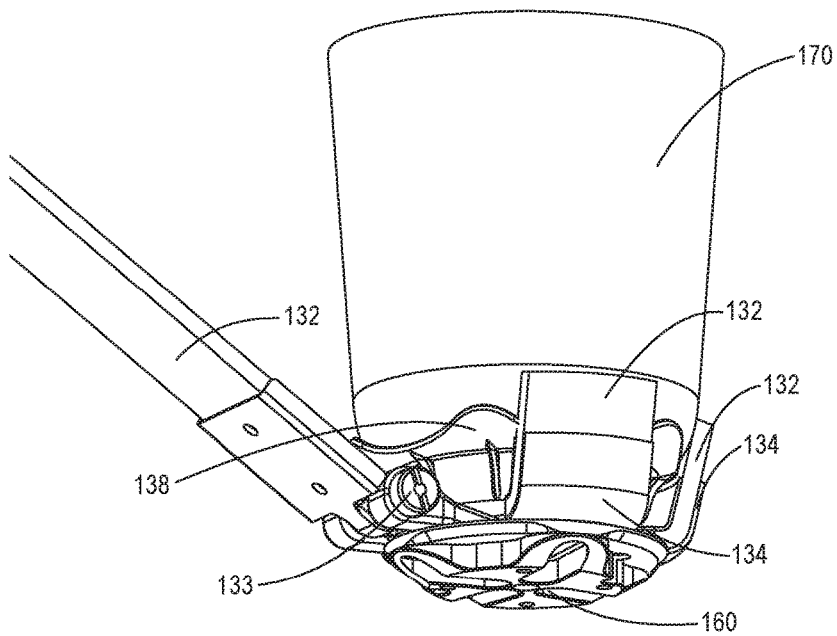
FIG. 14A is a bottom perspective view of a portion of an osseointegrated abutment support socket with a roll-on liner garment disposed above a percutaneous site protector support cup, showing, in particular, a strut connected to a distal base plate embodiment by way of a variable position hinge, the strut in an open position.
Figure 14B:
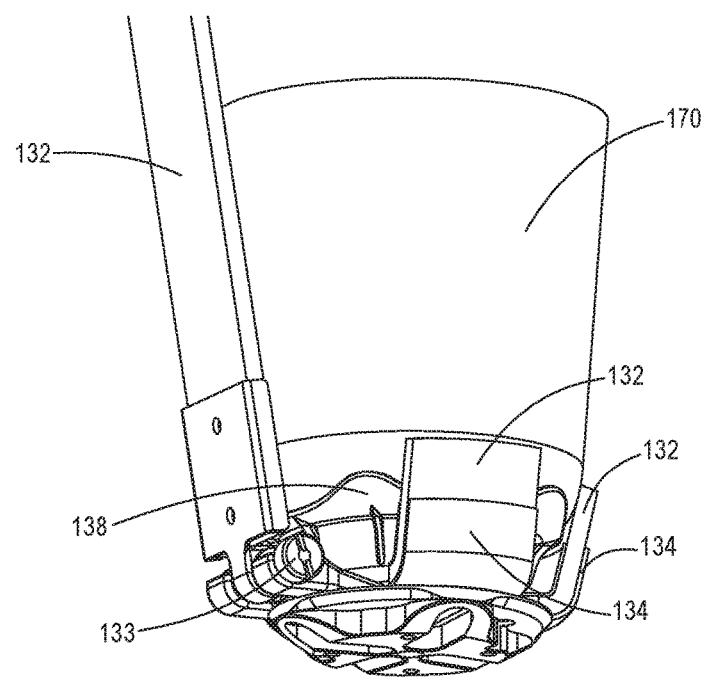
FIG. 14B is a bottom perspective view of a portion of an osseointegrated abutment support socket as in FIG. 14A, showing, in particular, a strut connected to a distal base plate embodiment by way of a variable position hinge, the strut in a full upright position.

FIG. 14A is a bottom perspective view of a portion of an OIAS socket 100 with a roll-on liner garment 170 disposed above a percutaneous site protector support cup 138, showing, in particular, a strut 132 connected to a distal base plate embodiment 160 by way of a variable position hinge 133, the strut in an open position. FIG. 14B is a bottom perspective view of a portion of an OIAS socket 100 as in FIG. 14A, showing, in particular, a strut 132 connected to a distal base plate embodiment by way of a variable position hinge 133, the strut in a full upright position.

Figure 14C:
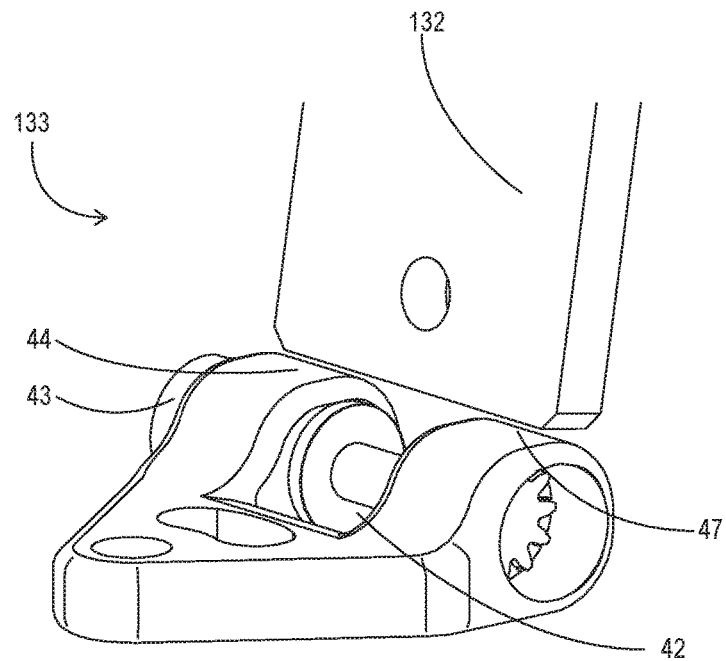
FIG. 14C is a top perspective detail view of a strut connector with a variable position hinge.
Figure 14D:
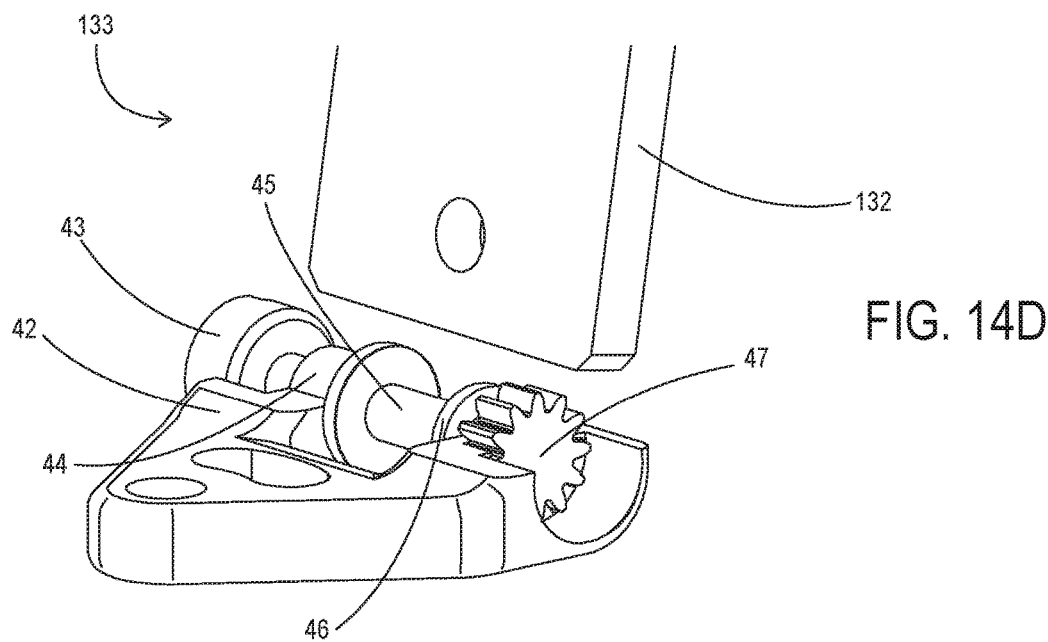
FIG. 14D is a top perspective view as in FIG. 14C but with an exposed view of the variable position hinge internal mechanism.

Embodiments of a strut connector with a variable position hinge are configured to freely permit inwardly directed deflection from the distal end of the strut, but allow external deflection of the strut only by way of a release button. These features are shown in detail in FIGS. 14C-14D with the strut connectors absent for clarity. FIG. 14C is a top perspective detail view of a strut connector 133 with a variable position hinge mechanism. FIG. 14D is a top perspective view (as in FIG. 14C) but with an exposed view of the variable position hinge internal mechanism that resides within hinge housing 42. The strut connector, as a whole is attachable to distal support base 150 by way bolts through base portion 41. Hinge housing 42 accommodates a one way bearing 45, a sleeve bearing 44, a Teflon washer 46, disposed between a release button 43 on one end and a lockable gear shaft 47 on the opposite end.

In one embodiment, a one-way hinge mechanism has a clutch system that uses a one-way bearing to bias rotation of the strut in one direction, inwards, to capture the residual limb. To release the strut, a user needs to push and hold the button to disengage the geared shaft from the hinge housing which allows the shaft and strut to rotate freely. When the button retracts due to the internal spring, the gear locates and seats in to the matching "gear" profile internal to the hinge housing. This locks the shaft and the one way bearing (clutch) restricts rotation of the strut in one direction once again.

Figure 15:
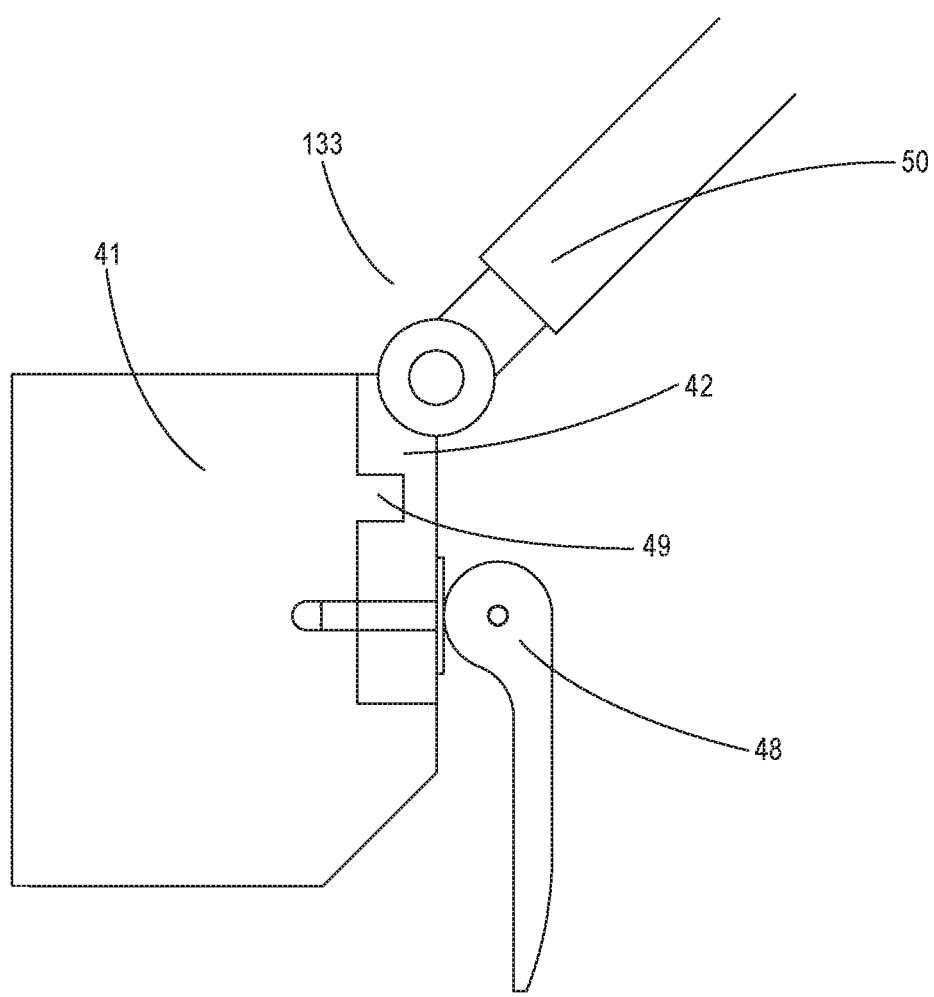
FIG. 15 is a side view of an alternative embodiment of an osseointegrated abutment support socket in which individual struts with a variable position hinge can be attached a distal base plate with a quick release mechanism.

FIG. 15 is a side view of portion of an alternative embodiment of an OIAS socket in which individual longitudinal struts 132 (having a strut hinge bracket 50) with a variable position hinge strut connector 133. Such a strut connector 133 can be attached a side of distal base plate 41 by way of a quick release mechanism that includes an indexing peg 49 on the side of distal base plate 41 that inserts into a slot within the strut connector, and which is secured by a cam lock mechanism 48. In a sense, this is stripped down version of an abutment support socket that includes such a modified base plate and four struts longitudinal 132 that can quickly be applied to (and removed from) a distal base that serves as a proximal connection of distal prosthetic components to a residual limb. This is an embodiment that could be used by a patient who, for example, in the course of normal activities of daily living does not wear a OIAS socket as described herein, but when engaging in high performance or physically demanding activity, would benefit from an additional level of abutment support.

In a medical device, such as a prosthetic socket, it can be appropriate to monitor aspects of the physical environment at sensor locations; for example, force, acceleration, and positional information can all be clinically informative and useful. Further, biometric parameters, such as temperature or humidity within a socket, or measurements of pulse, blood pressure, and EKG or electromyographic (EMG) activity can be informative and usefully applied to enhancing the clinically informative value of a device, such as a prosthetic socket.

Inasmuch as a functional purpose of an OIAS socket embodiment is to distribute load and torque away from the abutment, it is advantageous to quantify load and torque as they distribute through independently (1) directly through the abutment, and (2) through the support socket, bypassing the abutment. Accordingly, load and torsion sensors may be placed within the support socket at sites through which load and torque are conveyed. One or more sensors can be placed within a force path through which load and torsion are directed through the socket, exclusive of force paths through the abutment; and one or more sensors can be placed within a force path through which load and torsion are directed through the abutment, exclusive of force paths through the socket portion of the socket. Further in some embodiments, tension sensors may be placed within the paths of encircling tensioning bands that surround and compress the struts. Aspects of a sensor enabled OIAS socket 100 are further described in detail in U.S. Provisional Patent Application No. 62/364,930 of Pedtke et al., entitled "Prosthetic sockets that are sensor enabled to provide data for clinical use and mechanical adjustments" as filed on Jul. 21, 2016; the present application claims priority to this identified US Provisional Patent Application, and incorporates it into the present application in its entirety.

These sensors are typically disposed within a housing that includes a microprocessor and a signal transmitter, such transmitted signals being captured by a mobile phone or radio receiving device carried by the patient. From there, either signals or processed data may be further transmitted to another computer for storage and further analysis.

Transmitted data are processed into parameters such as total steps/day, load/step, total load/day, with associated statistics of distribution, and can be displayed and tracked over time. As data accumulate for any given patient, and for patient populations, it will become increasingly feasible to develop standards for safe and appropriate levels of load. Limits can be set, and alarms attached to particular critical parameters. The patient may also input relevant information, such as the type of activity being engaged in or the level of tension being applied to the OIAS socket.

A variable that the patient has control of is the tension being applied to encircling tensioning bands. It is anticipated that load distribution can be modulated or adjusted by tensioning adjustments; i.e., the application of increasing tension should move load onto the socket, thus bypassing the abutment.

Figure 16:
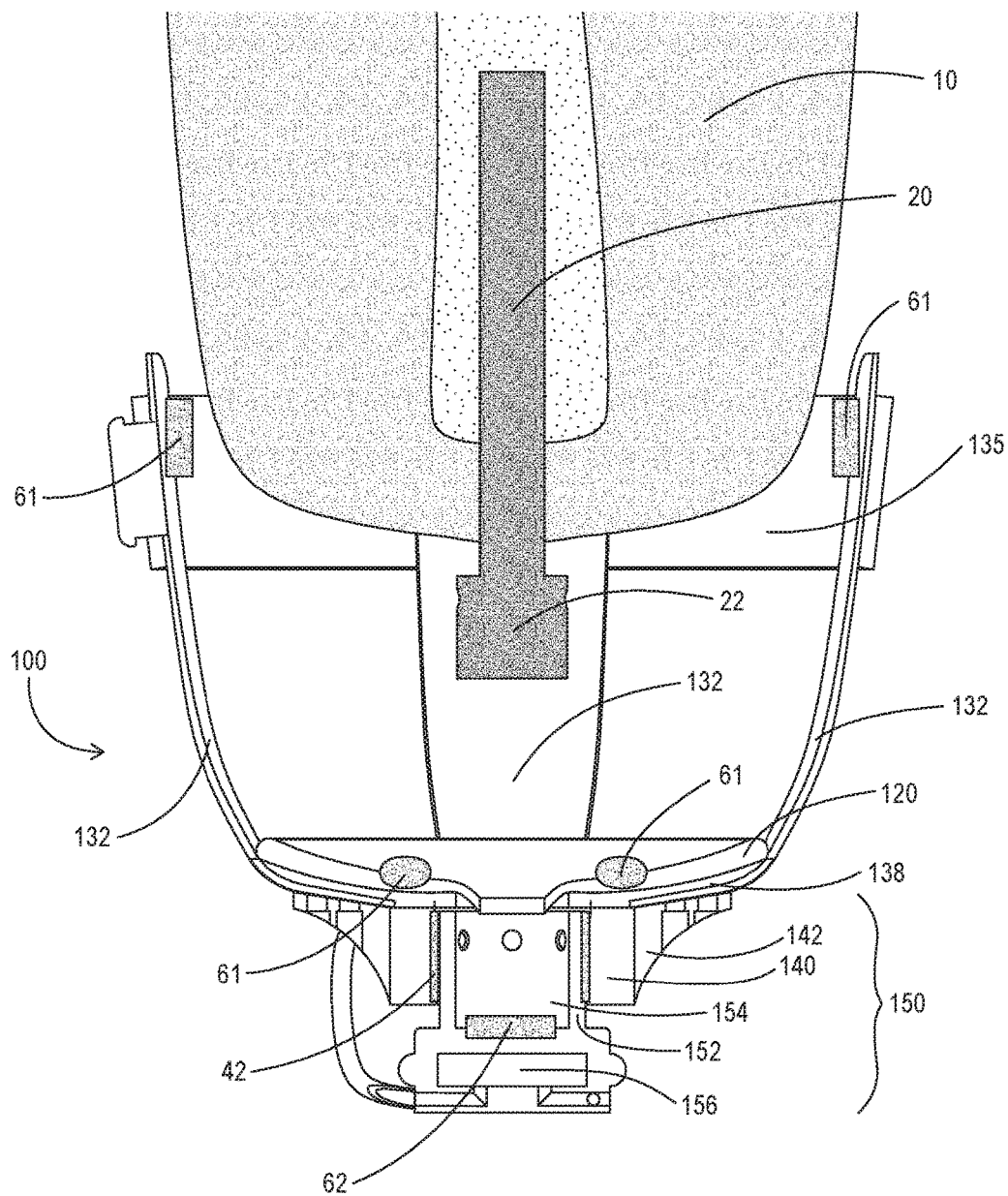
FIG. 16 is a side cross sectional view of a portion of an osseointegrated abutment support socket in which the residual limb and abutment are poised above the distal end of the proximal-facing cavity provided by the socket portion of the abutment support socket, showing, in particular sensors disposed at socket-residual limb interfaces and at an abutment-socket interface.

FIG. 16 is a side cross sectional view of a portion of an OIAS socket 100 in which the residual limb and abutment are poised above the distal end of the proximal-facing cavity provided by the socket portion of the abutment support socket, showing, in particular sensors 61 disposed at a socket-residual limb interface as well as sensors 62 disposed at an abutment-socket interface. Sensors 61 may be disposed (for example, as shown) internal to a proximal aspect of a longitudinal strut 132, as being tensioned by tensioning band 135, or positioned on a proximal aspect of strut support ring 140. These positions for a sensor can provide measurements of pressure or torsion applied by residual limb 10 directly on OIAS socket 100.

Sensors 42 may be disposed (for example, as shown) internal to a proximal aspect of a longitudinal strut 132, as being tensioned by tensioning band 135, or positioned on a proximal aspect of strut support ring 140. These positions for a sensor can provide measurements of pressure or torsion applied by residual limb 10 on osseointegrated support socket 100 through the distal end 22 of osseointegrated abutment 20.

Any one or more features of any embodiment may be combined with any one or more other features of any other embodiment, without departing from the scope of the invention. Further, the invention is not limited to the embodiments described or depicted herein for purposes of exemplification, but is to be defined only by a fair reading of claims appended to the patent application, including the full range of equivalency to which each element thereof is entitled. Further, while some theoretical considerations have been offered to provide an understanding of the technology (e.g., the effectiveness of a therapeutic intervention for a patient using an embodiment of the invention), the claims are not bound by such theory.

What is claimed is:

1. An osseointegrated abutment support socket for a residual limb in which an osseointegrated abutment has been implanted, the osseointegrated abutment support socket comprising:
   a distal socket base assembly, comprising:
      a base plate,
      a collar extending proximally from the base plate and forming a receptacle for receiving a distal end of the osseointegrated abutment, and
      a strut support ring disposed around the collar;
   multiple longitudinal struts connected at their distal ends to the strut support ring and extending proximally upward from the strut support ring;
   a percutaneous site protector coupled with at least one of the distal socket base assembly or the longitudinal struts, the percutaneous site protector configured to contact a distal surface of the residual limb near a percutaneous site where the distal end of the osseointegrated abutment exits the residual limb, the percutaneous site protector including an anti-infective measure to inhibit infection at the percutaneous site, wherein the anti-infective measure includes an antimicrobial agent or a bioactive agent;
   an evacuation chamber in the base plate of the distal socket base assembly; and
   a vacuum line fluidly connected with the evacuation chamber at one end and an opening in a proximal surface of the percutaneous site protector at an opposite end.

2. The osseointegrated abutment support socket of claim 1, wherein the multiple longitudinal struts comprise a thermoplastic fiber composite material.

3. The osseointegrated abutment support socket of claim 1, wherein the percutaneous site protector is configured to form a seal with the residual limb around the percutaneous site.

4. The osseointegrated abutment support socket of claim 1, further comprising a support cup disposed on an inner surface of the longitudinal struts, proximal to the distal socket base assembly, wherein the percutaneous site protector is disposed on the support cup.

5. The osseointegrated abutment support socket of claim 1, wherein the anti-infective measure comprises a proximal dressing layer.

6. The osseointegrated abutment support socket of claim 1, further comprising:
   at least one tensioning band disposed circumferentially around the longitudinal struts, closer to proximal ends of the longitudinal struts than to their distal ends; and
   a tension adjustment mechanism operatively connected to the at least one tensioning band.

7. The osseointegrated abutment support socket of claim 1, wherein the receptacle of the collar comprises an internal surface having a quick release feature adapted to complementarily engage a distal end of the osseointegrated abutment.

8. The osseointegrated abutment support socket of claim 7, wherein the quick release feature includes a ball bearing.

9. The osseointegrated abutment support socket of claim 1, wherein the strut support ring comprises multiple buttressed strut connectors configured to connect the longitudinal struts to the strut support ring.

10. The osseointegrated abutment support socket of claim 9, wherein at least one of the strut connectors comprises a directionally biased hinge mechanism.

11. The osseointegrated abutment support socket of claim 10, wherein the directionally biased hinge mechanism is configured to allow inward deflection of the longitudinal struts from a distal attachment site and outward deflection of the longitudinal struts by way of a release mechanism.

12. The osseointegrated abutment support socket of claim 1, further comprising at least one sensor coupled with the support socket and configured to sense at least one of a load or a torsion transferred from the osseointregated abutment to a portion of the abutment support socket.

13. The osseointegrated abutment support socket of claim 12, wherein the at least one sensor comprises a load sensor disposed within the socket, the load sensor comprising a transmitter configured to transmit sensed data.

14. The osseointegrated abutment support socket of claim 12, wherein the at least one sensor is attached to the percutaneous site protector.

15. The osseointegrated abutment support socket of claim 12, wherein the at least one sensor is attached to the distal socket base assembly.

16. The osseointegrated abutment support socket of claim 12, wherein the at least one sensor is attached to at least one of the longitudinal struts.

17. The osseointegrated abutment support socket according to claim 1, wherein the percutaneous site protector is adapted to surround the distal end of the osseointegrated abutment.

18. An osseointegrated abutment support socket for a residual limb in which an osseointegrated abutment has been implanted, the osseointegrated abutment support socket comprising:
   a distal socket base assembly, comprising:
      a base plate having an evacuation chamber,
      a collar extending proximally from the base plate and forming a receptacle for receiving a distal end of the osseointegrated abutment, the receptacle comprising a quick release feature with a ball bearing adapted to engage a distal end of the osseointegrated abutment, and
      a strut support ring disposed around the collar;
   multiple longitudinal struts connected at their distal ends to the strut support ring and extending proximally upward from the strut support ring;
   a percutaneous site protector coupled with at least one of the distal socket base assembly or the longitudinal struts, the percutaneous site protector configured to contact a distal surface of the residual limb near a percutaneous site where the osseointegrated abutment exits the residual limb.

19. An osseointegrated abutment support socket for a residual limb in which an osseointegrated abutment has been implanted, the osseointegrated abutment support socket comprising:
   a distal socket base assembly, comprising:
      a base plate having an evacuation chamber,
      a collar extending proximally from the base plate and forming a receptacle for receiving a distal end of the osseointegrated abutment, and
      a strut support ring disposed around the collar;
   multiple longitudinal struts connected at their distal ends to the strut support ring and extending proximally upward from the strut support ring;

a percutaneous site protector coupled with at least one of the distal socket base assembly or the longitudinal struts, the percutaneous site protector configured to contact a distal surface of the residual limb near a percutaneous site where the osseointegrated abutment exits the residual limb; and a vacuum line fluidly connected with the evacuation chamber of the base plate of the distal socket base assembly at one end and an opening in a proximal surface of the percutaneous site protector at an opposite end.

\* \* \* \* \*